US012691055B2

(12) United States Patent
Gopalrathnam et al.

(10) Patent No.: US 12,691,055 B2
(45) Date of Patent: Jul. 28, 2026

(54) INCRETIN ANALOG-CONTAINING COMPOSITIONS AND USES THEREOF

(71) Applicant: Eli Lilly and Company, Indianapolis, IN (US)

(72) Inventors: Ganapathy Gopalrathnam, Fishers, IN (US); Christopher Sears Minie, Zionsville, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 353 days.

(21) Appl. No.: 18/552,013

(22) PCT Filed: Mar. 22, 2022

(86) PCT No.: PCT/US2022/021309
§ 371 (c)(1),
(2) Date: Sep. 22, 2023

(87) PCT Pub. No.: WO2022/204117
PCT Pub. Date: Sep. 29, 2022

(65) Prior Publication Data

US 2024/0173250 A1 May 30, 2024

Related U.S. Application Data

(60) Provisional application No. 63/164,702, filed on Mar. 23, 2021.

(51) Int. Cl.

| | |
|---|---|
| ***A61K 9/00*** | (2006.01) |
| ***A61K 9/08*** | (2006.01) |
| ***A61K 38/26*** | (2006.01) |
| ***A61K 47/10*** | (2017.01) |
| ***A61K 47/26*** | (2006.01) |

(52) U.S. Cl.
CPC .............. *A61K 9/0019* (2013.01); *A61K 9/08* (2013.01); *A61K 38/26* (2013.01); *A61K 47/10* (2013.01); *A61K 47/26* (2013.01)

(58) Field of Classification Search
CPC ........ A61K 9/0019; A61K 9/08; A61K 38/26; A61K 47/10; A61K 47/26; A61P 3/10
See application file for complete search history.

(56) References Cited

U.S. PATENT DOCUMENTS

| | | | |
|---|---|---|---|
| 7,084,243 | B2 | 8/2006 | Glaesner et al. |
| 7,498,308 | B2 | 3/2009 | Glaesner et al. |
| 8,114,833 | B2 | 2/2012 | Pedersen et al. |
| 8,734,394 | B2 | 5/2014 | Adams et al. |
| 9,474,780 | B2 | 10/2016 | Bokvist et al. |
| 9,938,335 | B2 | 4/2018 | Mezo et al. |
| 11,357,820 | B2 | 6/2022 | Corvari et al. |
| 2009/0232807 | A1 | 9/2009 | Glaesner et al. |
| 2010/0196405 | A1 | 8/2010 | Ng |
| 2012/0329708 | A1 | 12/2012 | DiMarchi et al. |
| 2013/0164310 | A1 | 6/2013 | Annathur et al. |
| 2014/0073563 | A1 | 3/2014 | Boscheinen et al. |
| 2020/0024322 | A1 | 1/2020 | Abraham et al. |
| 2020/0331980 | A1 | 10/2020 | Alsina-Fernandez et al. |
| 2021/0221865 | A1 | 7/2021 | Alsina-Fernandez et al. |
| 2023/0203121 | A1 | 6/2023 | Alsina-Fernandez et al. |

FOREIGN PATENT DOCUMENTS

| | | | |
|---|---|---|---|
| WO | 2006110551 | A2 | 10/2006 |
| WO | 2008033888 | A2 | 3/2008 |
| WO | 2009024015 | A1 | 2/2009 |
| WO | 2011094337 | A1 | 8/2011 |
| WO | 2012025921 | A1 | 3/2012 |
| WO | 2018213151 | A1 | 11/2018 |
| WO | 2020023386 | | 1/2020 |

OTHER PUBLICATIONS

The International Search Report dated Jun. 24, 2022, issued by the European Patent Office for International Application No. PCT/US2022/021309.

Taiwan Office Action dated Feb. 4, 2023 for Taiwan Application No. 111109488.

Fransson, J., & Espander-Jansson, A. (1996). Local Tolerance of Subcutaneous Injections. Journal of Pharmacy and Pharmacology, 48(10), 1012-1015.

Laursen, T., Hansen, B., & Fisker, S. (2006). Pain Perception after Subcutaneous Injections of Media Containing Different Buffers. Basic & Clinical Pharmacology & Toxicology, 98(2), 218-221.

Millican, R.L., et al., Diabetes, Suppl., Abstract Book, A363 1504-P, 65th Scientific Sessions, NY col. 54 (Jun. 2005).

Saha, J. K., Xia, J., Millican, R., Grondin, J. M., Glaesner, W., & Jakubowski, J. A. (2007). DPP-4 Resistant Glucagon-Like Peptide-1 Analog LY548806: A Novel Agent for Control of Acute Hyperglycemia.

Williamson, A.; Hoggart,(2005)Pain: A review of three commonly used pain rating scales. Journal of Clinical Nursing, 14, (7), 798-804).

Yu, M., Benjamin, M. M., Srinivasan, S., Morin, E. E., Shishatskaya, E. I., Schwendeman, S. P., & Schwendeman, A. (2018). Battle of GLP-1 delivery technologies. Advanced drug delivery reviews, 130, 113-130.

*Primary Examiner* — Quanglong N Truong

(74) *Attorney, Agent, or Firm* — Matthew T. Lord

(57) ABSTRACT

A composition is provided that includes an incretin analog having activity at each the glucose-dependent insulinotropic polypeptide (GIP), glucagon-like peptide-1 (GLP-1) and glucagon (GCG) receptors (i.e., tri-receptor agonist) and one or more additional agents such as a tonicity agent and a preservative. Methods also are provided for treating diseases such as type 2 diabetes mellitus, dyslipidemia, metabolic syndrome, non-alcoholic fatty liver disease, non-alcoholic steatohepatitis and obesity with the composition.

25 Claims, No Drawings

Specification includes a Sequence Listing.

INCRETIN ANALOG-CONTAINING COMPOSITIONS AND USES THEREOF

The disclosure relates to compositions having an incretin analog with activity at each of a glucose-dependent insulinotropic polypeptide (GIP) receptor, glucagon-like peptide-1 (GLP-1) receptor and glucagon (GCG) receptor. The compositions additionally include agents that provide commercially acceptable shelf-life stability, in-use stability, and acceptable patient injection site experience. Such incretin analog-containing compositions can be used for treating conditions, diseases and disorders including diabetes mellitus (especially type 2 diabetes mellitus (T2DM)), dyslipidemia, metabolic syndrome, non-alcoholic fatty liver disease (NAFLD), non-alcoholic steatohepatitis (NASH) and/or obesity.

Over the past several decades, the prevalence of diabetes mellitus continues to rise, which is a chronic disorder characterized by hyperglycemia resulting from defects in insulin secretion, insulin action, or both. T2DM is the most common form of diabetes, accounting for about 90% of all diabetes. In T2DM, the combined effects of impaired insulin secretion and insulin resistance are associated with elevated blood glucose levels.

Uncontrolled diabetes can lead to one or more conditions that impact morbidity and mortality of such individuals. One of the main risk factors for T2DM is obesity, and many individuals with T2DM (~90%) are overweight or obese. It is documented that a decrease in body adiposity will lead to improvement in obesity-associated co-morbidities including hyperglycemia and cardiovascular events.

The current standard of care for T2DM includes diet and exercise, as well as treatment with oral medications and injectable glucose-lowering drugs including incretin-based therapies, such as GLP-1 receptor agonists and GIP/GLP-1 (GG) receptor agonists. Despite the treatment options available, significant numbers of individuals receiving approved therapies are not reaching glycemic control goals (see, e.g., Casagrande et al. (2013) *Diabetes Care* 36:2271-2279).

Intl. Patent Application Publication Nos. WO 2019/125929 and WO 2019/125938, as well as Intl. Patent Application No. PCT/US2020/064512 describe incretin analogs that act as GCG, GLP-1 and GIP (GGG) tri-receptor agonists and that can be used for treating T2DM. Therefore, there is a need for compositions including such GGG tri-receptor agonists having acceptable stability and acceptable injection site experience for an individual receiving the same for effective in glucose control and weight reduction in T2DM disease management.

To address this need, the disclosure first describes a pharmaceutically acceptable composition that includes an incretin analog, or a pharmaceutically acceptable salt thereof, a tonicity agent and optionally a preservative.

In some instances, the incretin analog can be SEQ ID NO:1 or a pharmaceutically acceptable salt thereof. In some instances, the incretin analog can be at a concentration from about 1 mg/mL to about 30 mg/mL. In certain instances, the incretin analog can be at a concentration of 1 mg/mL, 2 mg/mL, 3 mg/mL, 4 mg/mL, 5 mg/mL, 6 mg/mL, 8 mg/mL, 9 mg/mL, 12 mg/mL, 18 mg/mL, 24 mg/mL or 30 mg/mL. In some instances, pharmaceutically acceptable salts for use herein may be selected from sodium, trifluoroacetate, hydrochloride and/or acetate salts. In some instances, a pharmaceutically acceptable salt nay be a tetra sodium salt.

In some instances, the tonicity agent can be selected from glycerin, mannitol and propylene glycol. When the tonicity agent is glycerin, it can be at a concentration from about 5 mg/mL to about 50 mg/mL, especially 20 mg/mL. When the tonicity agent is mannitol, it can be at a concentration from about 10 mg/mL to about 100 mg/mL, especially 46 mg/mL. When the tonicity agent is propylene glycol, it can be at a concentration from about 5 mg/mL to about 50 mg/mL, especially 15 mg/mL. In certain instances, the tonicity agent is mannitol at 46 mg/mL.

In some instances, the preservative can be selected from m-cresol and phenol. When the preservative is m-cresol, it can be at a concentration from about 1 mg/mL to about 10 mg/mL, especially 3.15 mg/mL. When the preservative is phenol, it can be at a concentration from about 1 mg/mL to about 10 mg/mL, especially 5 mg/mL. In certain instances, the preservative is m-cresol at 3.15 mg/mL.

In some instances, the composition can be at a pH of about 7.0 to about 8.0, especially about 7.5. In certain instances, a buffer system can be used to maintain the pH, especially a TRIS buffer system at a concentration from about 10 mM to about 100 mM, especially 10 mM.

In view of the above, and in certain instances, the composition include an incretin analog at a concentration from about 2 mg/mL to about 30 mg/mL and a tonicity agent at a concentration from 10 to 50 mg/mL in a TRIS buffer system at a pH of about 7.5. In some instances, the incretin analog is SEQ ID NO:1. In some instances, the tonicity agent is mannitol at a concentration of 46 mg/mL. In some instances, the composition also includes a preservative such as m-cresol at a concentration from 3.15 mg/mL. In other instances, the composition also includes a preservative such as phenol at a concentration of 5.0 mg/mL.

The disclosure also describes methods of treating diabetes, where such methods include at least a step of administering to an individual in need an effective amount/dose of a composition herein. In some instances, the diabetes is T2DM. Alternatively, the disclosure describes methods of treating obesity, where such methods include at least a step of administering to an individual in need an effective amount of a composition herein. Alternatively, the disclosure describes methods of treating dyslipidemia, where such methods include at least a step of administering to an individual in need an effective amount/dose of a composition herein. Alternatively, the disclosure describes methods of treating fatty liver disease, where such methods include at least a step of administering to an individual in need an effective amount/dose of a composition herein. Alternatively, the disclosure describes methods of treating metabolic syndrome, where such methods include at least a step of administering to an individual in need an effective amount/dose of a composition herein. Alternatively, the disclosure describes methods of treating NAFLD, where such methods include at least a step of administering to an individual in need an effective amount/dose of a composition herein. Alternatively, the disclosure describes methods of treating NASH, where such methods include at least a step of administering to an individual in need an effective amount/dose of a composition herein. Alternatively, the disclosure describes methods providing therapeutic weight loss, where such methods include at least a step of administering to an individual in need an effective amount/dose of a composition herein. Alternatively, the disclosure describes methods providing non-therapeutic weight loss, where such methods include at least a step of administering to an individual in need an effective amount/dose of a composition herein. Alternatively, the disclosure describes methods of treating a condition mediated by GGG tri-receptor agonist activity, where such methods include at least a step of administering an effective amount of a composition herein to an individual in need an effective amount/dose of a composition herein.

In some instances, the composition is administered about once weekly. In other instances, the composition is administered once every seven days.

The disclosure further describes a composition herein for use as a medicament.

The disclosure further describes a composition herein for use in the treatment of diabetes. Alternatively, the disclosure describes a composition herein for use in the treatment of obesity. Alternatively, the disclosure describes a composition herein for use in providing therapeutic weight loss. Alternatively, the disclosure describes a composition herein for use in providing non-therapeutic weight loss.

The disclosure further describes an article of manufacture including a composition herein. In some instances, the article of manufacture is a multi-use vial. In some instances, the article of manufacture is a pre-filled syringe. In some instances, the article of manufacture is an automatic injection apparatus ("auto-injector"; see, e.g., U.S. Pat. No. 8,734,394). In some instances, the article of manufacture is a pump for continuous perfusion, especially a pump for subcutaneous infusion.

OVERVIEW

GCG is a twenty-nine amino acid hormone involved with the metabolism of amino acids, lipids and carbohydrates. GCG plays an important role in blood glucose regulation between meals, and overall body weight reduction. GLP-1 is an incretin hormone that stimulates insulin secretion and inhibits glucagon secretion. GIP is a gastric inhibitory peptide that exhibits a strong incretin effect on glucose-dependent secretion of insulin and has a known complementary effect with GLP-1 to improve glucose control and weight loss. Synergistic effects of a GGG tri-receptor agonist for these three receptors is postulated to result in a more potent, efficacious therapy than the current standard of care. The incretin analog of SEQ ID NO:1 is a fatty acid acylated, long-acting GGG tri-receptor agonist.

Unless defined otherwise, all technical and scientific terms used herein have the same meaning as commonly understood by one of skill in the art to which the disclosure pertains. Although any methods and materials similar to or equivalent to those described herein can be used in the practice or testing of the incretin analogs, pharmaceutical compositions and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Definitions

As used herein, "about" means within a statistically meaningful range of a value or values such as, for example, a stated concentration, length, molecular weight, pH, sequence identity, time frame, temperature or volume. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, and in reference to one or more of the GIP, GLP-1 or GCG receptors, "activity," "activate," "activating" and the like means a capacity of a compound, such as the incretin analogs herein, to bind to and induce a response at the receptor(s), as measured using assays known in the art, such as the in vitro assays described below.

As used herein, "amino acid" means a molecule that, from a chemical standpoint, is characterized by containing one or more amine groups and one or more carboxylic acid groups, and may contain other functional groups. As is known in the art, there is a set of twenty amino acids that are designated as standard amino acids and that are used as building blocks for most of the peptides/polypeptides/proteins produced by any living being.

As used herein, "analog" means a compound, such as a synthetic peptide or polypeptide, that activates a target receptor and that elicits at least one in vivo or in vitro effect elicited by a native receptor agonist.

As used herein, "chemical stability" means an ability of a therapeutic agent, substance or product to resist potential changes in composition in the product due to chemical reactions that may occur, such as isomerization, aggregation, oxidation, polymerization, fragmentation, and hydrolysis.

As used herein, "effective amount" means an amount, concentration or dose of one or more of the incretin analogs herein, or a pharmaceutically acceptable salt thereof which, upon single or multiple dose administration to an individual in need thereof, provides a desired effect in such an individual under diagnosis or treatment (i.e., may produce a clinically measurable difference in a condition of the individual such as, for example, a reduction in blood glucose, a reduction in HbA1c, a reduction in weight or body fat and/or a change body composition). An effective amount can be readily determined by one of skill in the art by using known techniques and by observing results obtained under analogous circumstances. In determining the effective amount for an individual, a number of factors are considered, including, but not limited to, the species of mammal, its size, age and general health, the specific disease or disorder involved, the degree of or involvement or the severity of the disease or disorder, the response of the individual, the particular incretin analog administered, the mode of administration, the bioavailability characteristics of the preparation administered, the dose regimen selected, the use of concomitant medication, and other relevant circumstances.

As used herein, "half-maximal effective concentration" or "$EC_{50}$" means a concentration of compound that results in 50% activation/stimulation of an assay endpoint, such as a dose-response curve (e.g., cAMP).

As used herein, "incretin analog" means a compound having structural similarities with, but multiple differences from, each of GIP, GLP-1 and GCG, especially human GIP, human GLP-1 and human GCG. The incretin analogs herein include amino acid sequences resulting in the compounds having affinity for and activity at each of the GIP, GLP-1 and GCG receptors (i.e., triple receptor agonist activity). Exemplary incretin analogs and sequences for human GIP, GLP-1 and GCG for use herein are described in Intl. Patent Application Publication Nos. WO 2019/125929 and WO 2019/125938, as well as Intl. Patent Application No. PCT/US2020/064512. Of particular use herein is Example 12 of Intl. Patent Application Publication No. WO 2019/125938, which has the following sequence:

$YX_2QGTFTSDYSIX_{13}LDKX_{17}AX_{19}X_{20}AFIEYLLX_{28}X_{29}GPSSX_{34}APPPS$, where $X_2$ is Aib, $X_{13}$ is αMeL, $X_{17}$ is K, $X_{19}$ is Q, $X_{20}$ is Aib, $X_{28}$ is E, $X_{29}$ is G and $X_{34}$ is G, where the K at $X_{17}$ is chemically modified through conjugation to the epsilon amino group of the K side-chain with (2-[2-(2-aminoethoxy)-ethoxy]-acetyl)-(γGlu)-CO—$(CH_2)_{18}CO_2H$, and where the C-terminal amino acid is amidated as a C-terminal primary amide (SEQ ID NO:1).

Below is a depiction of the structure of the incretin analog of SEQ ID NO:1 using the standard single letter amino acid codes with the exception of residues Aib2, αMeL13, K17 and Aib20, where the structures of these amino acid residues have been expanded:

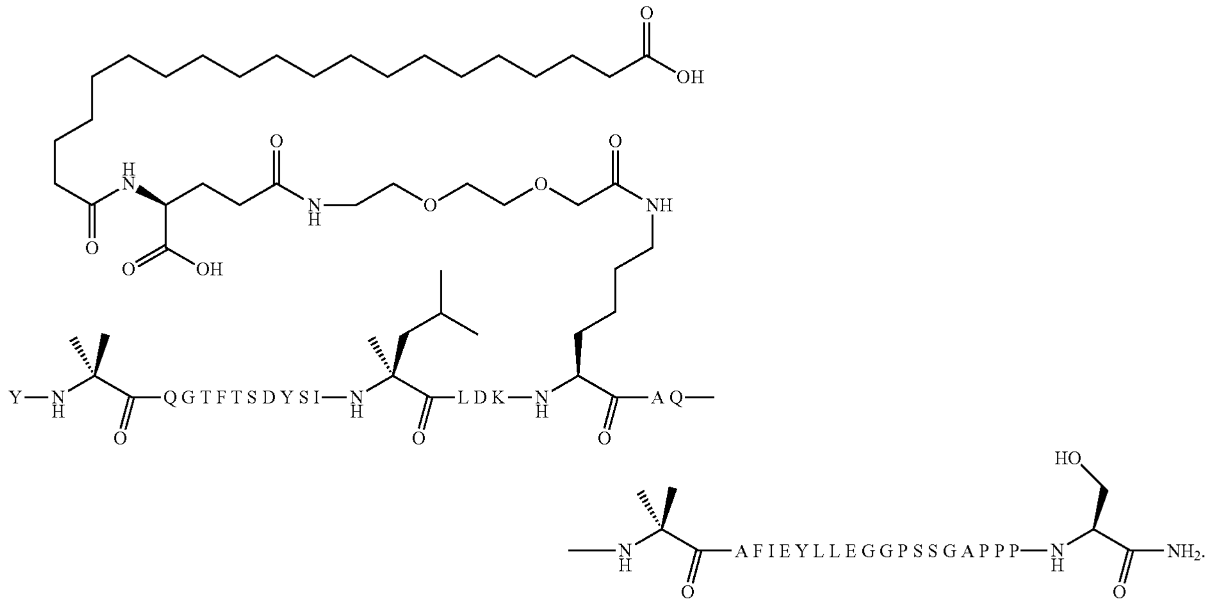

As used herein, "individual in need thereof" means a mammal, such as a human, with a condition, disease, disorder or symptom requiring treatment or therapy, including for example, those listed herein. In particular, the preferred individual to be treated is a human.

As used herein, "long-acting" means that binding affinity and activity of an incretin analog herein continues for a period of time greater than a reference peptide such as native, human GIP (SEQ ID NO:2), human GLP-1 (SEQ ID NO:3) and/or human GCG (SEQ ID NO:4), allowing for dosing at least as infrequently as once-daily, thrice-weekly, twice-weekly, once-weekly or even monthly. The time action profile of the incretin analogs herein may be measured using known pharmacokinetic methods such as those described in the Examples below.

As used herein, "microbiological stability" means an ability of a therapeutic agent, substance or product to maintain its sterility when exposed to environmental or other microorganisms.

As used herein, "non-standard amino acid" means an amino acid that may occur naturally in cells but does not participate in peptide synthesis. Non-standard amino acids can be constituents of a peptide and can be generated by modifying standard amino acids in the peptide (i.e., via post-translational modification). Non-standard amino acids can include D-amino acids, which have an opposite absolute chirality of the standard, L-amino acids above.

As used herein, "pharmaceutically acceptable salt" is well known to one of skill in the art. Pharmaceutically acceptable salts and common techniques for preparing them are well known in the art (see, e.g., Stahl et al., Handbook of Pharmaceutical Salts: Properties, Selection and Use, 2nd Revised Edition (Wiley-V C H, 2011)). Pharmaceutically acceptable salts for use herein include sodium, trifluoroacetate, hydrochloride and/or acetate salts.

As used herein, "physical stability" means an ability of a therapeutic agent, substance or product to maintain its physical dimensions and properties when exposed to conditions normally encountered in its service environment such as, for example, agitation and shear.

As used herein, "propylene glycol" is well known to one of skill in the art and is represented by the formula: $C_3H_8O_2$.

As used herein, "saturated" means that a fatty acid moiety that contains no carbon-carbon double or triple bonds.

As used herein, "shelf-life stability" means a time necessary for a therapeutic agent, such as an incretin analog herein, to decay to about 90% of its original concentration. Shelf-life stability also means a time a therapeutic agent t will remain stable when stored under recommended storage conditions such as, for example, as measured under controlled conditions at about 5° C.

As used herein, "therapeutic agent stability" means an extent to which a therapeutic agent or substance or product retains, within specified limits and throughout its period of storage and use, the same properties and characteristics that it possessed at the time of its manufacture. Exemplary properties for therapeutic agent stability that can be assessed include, but are not limited to, chemical, physical, microbiological, therapeutic and/or toxicological properties thereof. Factors that can affect therapeutic agent stability include, but are not limited to, concentration, dosage form, light, moisture, oxygen, pH and temperature.

As used herein, "treat," "treating," "to treat" and the like mean restraining, slowing, stopping or reversing the progression or severity of an existing condition, disease, disorder or symptom.

As used herein, and with reference to an incretin analog, "triple receptor agonist activity" means an incretin analog with activity at each of the GIP, GLP-1 and GCG receptors, especially an analog having a balanced and sufficient activity at each receptor to provide the benefits of agonism of that receptor while avoiding unwanted side effects associated with too much activity of that receptor. Moreover, the incretin analogs having triple receptor agonist activity have extended duration of action at each of the GIP, GLP-1 and GCG receptors, which advantageously allows for dosing as infrequently as once-a-day, thrice-weekly, twice-weekly or once-a-week.

Certain abbreviations are defined as follows: "Aib" refers to α-aminoisobutyric acid; "αMeL" refers to α-methyl leucine; "αMeK" refers to α-methyl lysine; "αMeF" refers to α-methyl phenylalanine; "αMeF(2F)" refers to α-methyl 2-fluoropheynylalanine; "αMeY" refers to α-methyl tyrosine; "EDTA" refers to ethylenediaminetetraacetic acid; "HIAC" refers to high accuracy liquid particle counting by light obscuration technique; "hr" refers to hour or hours; "IV" refers to intravenous; "Iva" refers to isovaline; "kDa" refers to kilodaltons; "LC-MS" refers to liquid chromatography-mass spectrometry; "MFI" refers to microflow imaging; "min" refers to minute or minutes; "MS" refers to mass spectrometry; "Orn" or "O" refers to ornithine; "RP-HPLC" refers to reversed-phase high performance liquid chromatography; "sec" refers to second or seconds; "SEM" refers to standard error of the mean; "SPA" refers to scintillation proximity assay; "SQ" refers to subcutaneous; "TFA" refers to trifluoroacetic acid; "tBu" refers to tert-butyl; "TRIS" refers to tris(hydroxymethyl)aminomethane; and "Trt" refers to Trityl.

COMPOSITIONS

The compositions herein include an incretin analog of, for example, SEQ ID NO:1 or a pharmaceutically acceptable salt thereof, at a concentration from about 1 mg/mL to about 30 mg/mL. In some instances, the concentration of the incretin analog can be from about 2 mg/mL to about 29 mg/mL, about 3 mg/mL to about 28 mg/mL, about 4 mg/mL to about 27 mg/mL, about 5 mg/mL to about 26 mg/mL, about 6 mg/mL to about 25 mg/ml, about 7 mg/mL to about 24 mg/mL, about 8 mg/mL to about 23 mg/mL, about 9 mg/mL to about 22 mg/mL, about 10 mg/mL to about 21 mg/mL, about 11 mg/mL to about 20 mg/mL, about 12 mg/mL to about 19 mg/mL, about 13 mg/mL to about 18 mg/mL, about 14 mg/mL to about 17 mg/mL or about 15 mg/mL to about 16 mg/mL. In other instances, the concentration of the incretin analog can be about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL or about 30 mg/mL. In certain instances, the concentration of the incretin analog can be 1 mg/mL, 2 mg/mL, 3 mg/mL, 4 mg/mL, 5 mg/mL, 6 mg/mL, 8 mg/mL, 9 mg/mL, 10 mg/mL, 12 mg/mL, 18 mg/mL, 24 mg/mL or 30 mg/mL.

In some instances, the dose range can be from about 0.5 mg to about 15 mg. In other instances, the dose range can be from about 6 mg to about 24 mg.

The incretin analogs can be recombinantly produced or synthetically produced (see, e.g., Intl. Patent Application Publication Nos. WO 2019/125929, WO 2019/125938, as well as Intl. Patent Application No. PCT/US2020/064512).

In addition to the above, the compositions herein also include a tonicity agent to render an isotonic formulation, suitable for subcutaneous administration. Exemplary tonicity agents include, but are not limited to, glycerin, mannitol and propylene glycol, or a combination thereof. In some instances, the tonicity agent is mannitol.

When the tonicity agent is glycerin, it can be at a concentration from about 5 mg/mL to about 50 mg/mL, especially 20 mg/mL.

When the tonicity agent is mannitol, it can be at a concentration from about 10 mg/mL to about 100 mg/mL, especially 46 mg/mL.

When the tonicity agent is propylene glycol, it can be at a concentration from about 5 mg/mL to about 50 mg/mL, especially 15 mg/mL.

Buffer System

In addition to the above, the compositions also can include a buffer system to maintain a proper pH. Exemplary buffer systems include, but are not limited to, phosphate ($PO_4$) buffer and TRIS buffer, especially TRIS.

When the buffer system is TRIS, it can be at a concentration from about 10 mM to about 100 mM, especially 10 mM.

Regardless of the buffer system, the pH of the composition can be from about 7.0 to about 8.0, especially 7.5. In some instances, the pH is from about 7.1 to about 7.9, from about 7.2 to about 7.8, from about 7.3 to about 7.7, from about 7.4 to about 7.6, or about 7.5. In other instances, the pH of the composition is about 7.0, about 7.1, about 7.2, about 7.3, about 7.4, about 7.5, about 7.6, about 7.7, about 7.8, about 7.9 or about 8.0.

Preservatives

The compositions herein are sterile when first produced. As such, the compositions optionally can include a preservative that is compatible with the other components of the composition and that may be added at sufficient strength to meet applicable regulatory anti-microbial preservative requirements. Pharmaceutically acceptable preservatives are known to one of skill in the art (see, e.g., Remington: The Science and Practice of Pharmacy (Troy, Ed., 21st Edition, Lippincott, Williams & Wilkins, 2006).

In view of the above, the compositions also can include a preservative to maintain sterility. Exemplary preservatives include, but are not limited to, m-cresol and phenol, especially m-cresol.

When the preservative is m-cresol, it can be at a concentration from about 1 mg/mL to about 10 mg/mL, especially 3.15 mg/mL.

When the preservative is phenol, it can be at a concentration from about 1 mg/mL to about 10 mg/mL, especially 5.0 mg/mL.

Packaging/Delivery Devices

The compositions herein can be administered intravenously (IV), intramuscularly (IM) or subcutaneously (SQ). The compositions typically are administered using a pre-filled, disposable pen, reusable pen, or automatic pen injector. Alternatively, the compositions may be administered using a multi-use vial or a pump device. In some instances, the device is an automatic injection apparatus as described in U.S. Pat. No. 8,734,394.

The compositions herein therefore may be presented in a pre-filled syringe/multi-use vial. Such pre-filled syringe/multi-use vial may be useful for administering about 0.5 mL to about 1 mL of the composition per patient per dose. The dose of the composition may be administered using a dosing schedule determined by a clinician, physician or other trained medical professional.

Alternatively, the composition can be prepared for a cartridge and therefore will differ from the above composition by including a preservative.

Alternatively, the composition can be prepared as part of an article of manufacture comprising the composition, where the article of manufacture can be a multi-use vial, a reusable pen injector, a pre-filled, disposable pen, an autoinjector or a pump.

In view of the above, the compositions herein are associated with acceptable shelf-life stability, in-use stability and acceptable injection site experience.

METHODS

The incretin analogs described herein may be used for treating a variety of conditions, disorders, diseases or symptoms. For example, the incretin analogs described herein may be used for treating diabetes mellitus (especially T2DM), dyslipidemia, metabolic syndrome, NAFLD, NASH and/or obesity. In particular, methods are provided for treating T2DM in an individual, where such methods include at least a step of administering to an individual in need of such treatment an effective amount of an incretin analog described herein, or a pharmaceutically acceptable salt thereof.

Additionally, methods are provided for treating obesity in an individual, where such methods include at least a step of administering to an individual in need of such treatment an effective amount of an incretin analog described herein, or a pharmaceutically acceptable salt thereof.

Additionally, methods are provided for inducing non-therapeutic weight loss in an individual, where such methods include at least a step of administering to an individual in need of such treatment an effective amount of an incretin analog described herein, or a pharmaceutically acceptable salt thereof.

Additionally, methods are provided for treating metabolic syndrome in an individual, where such methods include at least a step of administering to an individual in need of such treatment an effective amount of an incretin analog described herein, or a pharmaceutically acceptable salt thereof.

Additionally, methods are provided for treating NASH in an individual, where such methods include at least a step of administering to an individual in need of such treatment an effective amount of an incretin analog described herein, or a pharmaceutically acceptable salt thereof.

Additionally, methods are provided for treating NAFLD in an individual, where such methods include at least a step of administering to an individual in need of such treatment an effective amount of an incretin analog described herein, or a pharmaceutically acceptable salt thereof.

In these methods, effectiveness of the composition can be assessed by, for example, observing a significant reduction in blood glucose, observing a significant increase in insulin, observing a significant reduction in HbA1c and/or observing a significant reduction in body weight.

EXAMPLES

The following non-limiting examples are offered for purposes of illustration, not limitation.

Formulations

Example 1: Compositions Containing an Incretin Analog, a Tonicity Agent and an Optional Preservative Compositions are prepared substantially as described herein. Such compositions include an incretin analog of SEQ ID NO:1 at 2, 6 or 10 mg/mL and additional ingredients as set forth in Table 1. The preservative and tonicity agent effects are studied by varying each type at fixed concentrations. Preservative concentrations are fixed at 3.15 mg/mL and 5 mg/mL m-cresol and phenol, respectively. Tonicity agent concentrations are selected to render an isotonic formulation suitable for subcutaneous administration.

Solutions are prepared by adding the incretin analog of SEQ ID NO:1 into an appropriate matrix, mixing until dissolution into a solution is achieved, and then the solution is brought to final volume using a volumetric flask of an appropriate size. Each formulation solution is aseptically filtered with 0.22-μm PVDF filters and filled into 5 mL glass vials, at a 3 mL fill volume.

TABLE 1

Exemplary formulations.

| Formulation No. | Buffer pH (10 mM) | Preservative | Tonicity Agent | Tonicity Agent (mg/mL) | Incretin Analog (mg/mL) |
|---|---|---|---|---|---|
| 1 | 7.5 Tris | m-cresol | mannitol | 46 | 2 |
| 2 | | m-cresol | propylene glycol | 15 | 6 |
| 3 | | m-cresol | glycerin | 20 | 10 |
| 4 | | phenol | propylene glycol | 15 | 2 |
| 5 | | m-cresol | propylene glycol | 15 | 10 |
| 6 | | m-cresol | glycerin | 20 | 2 |
| 7 | | m-cresol | propylene glycol | 15 | 10 |
| 8 | | phenol | glycerin | 20 | 10 |
| 9 | | m-cresol | mannitol | 46 | 10 |
| 10 | | phenol | mannitol | 46 | 2 |
| 11 | | phenol | mannitol | 46 | 10 |
| 12 | | m-cresol | propylene glycol | 15 | 2 |
| 13 | | phenol | glycerin | 20 | 2 |
| 14 | | phenol | propylene glycol | 15 | 6 |

TABLE 1-continued

| Exemplary formulations. | | | | | | |
|---|---|---|---|---|---|---|
| Formulation No. | pH | Buffer (10 mM) | Preservative | Tonicity Agent | Tonicity Agent (mg/mL) | Incretin Analog (mg/mL) |
| 15 | 7 | $PO_4$ | m-cresol | mannitol | 46 | 6 |
| 16 | 8 | $PO_4$ | phenol | | | |
| 17 | 8 | $PO_4$ | m-cresol | | | |
| 18 | 7 | $PO_4$ | phenol | | | |
| 19 | 7.5 | Tris | — | | | |
| 20 | 7.5 | Tris | — | mannitol/EDTA | 46/0.3 | 6 |
| 21 | 7.5 | Tris | m-cresol | mannitol/EDTA | 46/0.3 | 6 |

Samples are stored at 5° C., 30° C. or 40° C. for further studies as described in the subsequent Examples.

In Vitro Data (Chemical and Physical Stability)

Example 2: In-Use Stability Studies

Stability-indicating analytical and characterization techniques selected to measure the chemical and physical stability of the formulations include size exclusion chromatography (SEC), reversed phase high performance liquid chromatography (RP-HPLC) and visual appearance.

A sampling schedule is outlined in Table 2. A model is employed to extrapolate trends out to 24 months at the nominal storage temperature of 5° C. with an additional 1 month at 30° C. for in-use. Zero-order Arrhenius modeling is used for SEC (monomer, aggregates) and RP-HPLC (purity).

TABLE 2

| Sampling schedule. | | | | |
|---|---|---|---|---|
| Storage | Time (weeks) | | | |
| Condition (° C.) | 0 | 2 | 4 | 8 |
| 5 | X | — | X | X |
| 30 | X | X | X | X |
| 40 | X | X | X | X |

X = sample time point

SEC: an isocratic size exclusion HPLC method with UV detection at 214 nm is used and is designed to determine relative amounts of incretin analog monomer and total aggregates. Monomer and aggregates are reported as peak area percent to the total area. The procedure is stability indicating as measured by its ability to resolve known impurities from the incretin analog. The results of the stability study are shown in Table 3, which shows the percent monomer values of select formulations of Table 1 at the 5° C., 30° C. and 40° C. storage conditions. Stability data are available for up to 8 weeks of storage.

TABLE 3

| SEC percent monomer (% peak area) of exemplary formulations. | | | | | |
|---|---|---|---|---|---|
| Formulation | Temp | Percent Monomer (%) Time (weeks) | | | |
| No. | (° C.) | 0 | 2 | 4 | 8 |
| 1 | 5 | 98.7 | | 98.8 | 98.9 |
| | 30 | | 98.9 | 98.6 | 96.1 |
| | 40 | | 98.7 | 97.9 | 97.5 |

TABLE 3-continued

| SEC percent monomer (% peak area) of exemplary formulations. | | | | | |
|---|---|---|---|---|---|
| Formulation | Temp | Percent Monomer (%) Time (weeks) | | | |
| No. | (° C.) | 0 | 2 | 4 | 8 |
| 2 | 5 | 99.0 | | 98.7 | 98.9 |
| | 30 | | 98.5 | 98.5 | 98.6 |
| | 40 | | 98.6 | 98.2 | 97.9 |
| 3 | 5 | 98.8 | | 98.8 | 99.0 |
| | 30 | | 98.9 | 98.6 | 98.6 |
| | 40 | | 98.8 | 98.2 | 97.6 |
| 4 | 5 | 99.1 | | 98.6 | 98.8 |
| | 30 | | 98.9 | 98.8 | 98.6 |
| | 40 | | 98.7 | 98.4 | 97.9 |
| 5 | 5 | 98.9 | | 98.8 | 98.9 |
| | 30 | | 98.9 | 98.6 | 98.7 |
| | 40 | | 98.8 | 98.3 | 97.9 |
| 6 | 5 | 99.0 | | 98.7 | 98.9 |
| | 30 | | 98.7 | 98.5 | 98.5 |
| | 40 | | 98.7 | 98.0 | 97.8 |
| 7 | 5 | 99.0 | | 98.5 | 99.0 |
| | 30 | | 98.8 | 98.7 | 98.2 |
| | 40 | | 98.4 | 98.2 | 97.8 |
| 8 | 5 | 99.0 | | 98.7 | 99.0 |
| | 30 | | 98.9 | 98.6 | 98.8 |
| | 40 | | 98.6 | 98.2 | 97.9 |
| 9 | 5 | 99.1 | | 98.3 | 99.0 |
| | 30 | | 98.8 | 98.4 | 98.6 |
| | 40 | | 98.7 | 98.1 | 97.4 |
| 10 | 5 | 98.9 | | 98.4 | 99.0 |
| | 30 | | 98.7 | 98.7 | 98.5 |
| | 40 | | 98.5 | 98.3 | 97.8 |
| 11 | 5 | 98.9 | | 98.5 | 98.9 |
| | 30 | | 98.7 | 98.7 | 98.3 |
| | 40 | | 98.7 | 98.3 | 97.7 |
| 12 | 5 | 98.8 | | 98.5 | 98.9 |
| | 30 | | 98.9 | 98.7 | 98.6 |
| | 40 | | 98.6 | 98.2 | 97.9 |
| 13 | 5 | 99.0 | | 98.6 | 99.0 |
| | 30 | | 98.9 | 98.6 | 98.6 |
| | 40 | | 98.9 | 98.3 | 97.9 |
| 14 | 5 | 99.1 | | 98.7 | 99.0 |
| | 30 | | 98.6 | 98.7 | 98.8 |
| | 40 | | 98.9 | 98.5 | 97.9 |
| 19 | 5 | 99.1 | | 98.5 | 99.0 |
| | 30 | | 99 | 98.6 | 98.8 |
| | 40 | | 98.8 | 98.5 | 98.2 |

Increasing temperature results in decreased monomer purity after 8 weeks. As shown in Table 4, there is essentially no change in monomer purity after 8 weeks at 5° C., with monomer purity decreasing as a function of temperature. The SEC results from formulation 1 (m-cresol/mannitol) at the 8-week time point, 30° C., are about 1% lower than the SEC results at the 8-week time point, 40° C. These data suggest an anomaly and therefore the 8-week, 30° C. condition data for formulation 1 are excluded from model predictions. Data from all other conditions are used for stability modeling, assuming Arrhenius kinetics.

TABLE 4

SEC percent monomer predicted values after 24 months at 5° C. plus 1 month at 30° C.

| Formulation No. | Percent Monomer (%) |
|---|---|
| 1 | 98.2 |
| 2 | 98.4 |
| 3 | 98.4 |
| 4 | 98.6 |
| 5 | 98.5 |
| 6 | 98.4 |
| 7 | 98.4 |
| 8 | 98.5 |
| 9 | 98.4 |
| 10 | 98.4 |
| 11 | 98.3 |
| 12 | 98.4 |
| 13 | 98.6 |
| 14 | 98.7 |
| 19 | 98.7 |

A formulation factor trends for aggregates over the design region studied closely follows those of monomer purity. Table 5 shows the total aggregates increasing as a function of temperature. Table 6 shows effects of the input variables on predicted change and predicted values of % total aggregates over 24 months at 5° C. plus 1 month at 30° C. Input variables do not impact aggregates by SEC significantly.

TABLE 5

SEC total aggregates (%) of exemplary formulations.

| Formulation | Condition | Total Aggregates (%) Time (weeks) | | | |
|---|---|---|---|---|---|
| No. | (° C.) | 0 | 2 | 4 | 8 |
| 1 | 30 | 0.7 | 0.5 | 0.8 | 2.9 |
| | 40 | | 0.4 | 1.1 | 0.6 |
| | 5 | | | 0.7 | 0.5 |
| 2 | 30 | 0.4 | 0.9 | 0.9 | 0.5 |
| | 40 | | 0.6 | 0.9 | 0.6 |
| | 5 | | | 0.8 | 0.5 |
| 3 | 30 | 0.6 | 0.4 | 0.8 | 0.6 |
| | 40 | | 0.4 | 0.8 | 0.6 |
| | 5 | | | 0.7 | 0.4 |
| 4 | 30 | 0.4 | 0.5 | 0.6 | 0.5 |
| | 40 | | 0.5 | 0.8 | 0.8 |
| | 5 | | | 0.9 | 0.6 |
| 5 | 30 | 0.6 | 0.4 | 0.8 | 0.6 |
| | 40 | | 0.4 | 0.8 | 0.6 |
| | 5 | | | 0.8 | 0.5 |
| 6 | 30 | 0.4 | 0.7 | 0.8 | 0.6 |
| | 40 | | 0.5 | 1 | 0.6 |
| | 5 | | | 0.8 | 0.5 |
| 7 | 30 | 0.4 | 0.5 | 0.7 | 1 |
| | 40 | | 0.8 | 0.9 | 0.6 |
| | 5 | | | 0.9 | 0.4 |
| 8 | 30 | 0.5 | 0.5 | 0.9 | 0.5 |
| | 40 | | 0.6 | 0.9 | 0.7 |
| | 5 | | | 0.8 | 0.4 |
| 9 | 30 | 0.4 | 0.5 | 1 | 0.5 |
| | 40 | | 0.5 | 0.9 | 0.6 |
| | 5 | | | 1.2 | 0.5 |
| 10 | 30 | 0.5 | 0.6 | 0.7 | 0.7 |
| | 40 | | 0.7 | 0.8 | 0.6 |
| | 5 | | | 1.1 | 0.5 |
| 11 | 30 | 0.5 | 0.6 | 0.7 | 0.9 |
| | 40 | | 0.5 | 0.8 | 0.7 |
| | 5 | | | 1 | 0.5 |

TABLE 5-continued

SEC total aggregates (%) of exemplary formulations.

| Formulation | Condition | Total Aggregates (%) Time (weeks) | | | |
|---|---|---|---|---|---|
| No. | (° C.) | 0 | 2 | 4 | 8 |
| 12 | 30 | 0.6 | 0.4 | 0.7 | 0.6 |
| | 40 | | 0.6 | 0.9 | 0.6 |
| | 5 | | | 1 | 0.5 |
| 13 | 30 | 0.4 | 0.4 | 0.8 | 0.6 |
| | 40 | | 0.4 | 0.8 | 0.7 |
| | 5 | | | 0.9 | 0.5 |
| 14 | 30 | 0.4 | 0.8 | 0.7 | 0.5 |
| | 40 | | 0.3 | 0.7 | 0.8 |
| | 5 | | | 0.8 | 0.5 |
| 19 | 30 | 0.3 | 0.4 | 0.9 | 0.5 |
| | 40 | | 0.5 | 0.8 | 0.6 |
| | 5 | | | 1 | 0.4 |

TABLE 6

SEC percent total aggregates predicted values after 24 months at 5° C. plus 1 month at 30° C.

| Formulation No. | Percent Total Aggregates (%) |
|---|---|
| 1 | 0.8 |
| 2 | 0.8 |
| 3 | 0.8 |
| 4 | 0.7 |
| 5 | 0.7 |
| 6 | 0.8 |
| 7 | 0.8 |
| 8 | 0.7 |
| 9 | 0.8 |
| 10 | 0.7 |
| 11 | 0.7 |
| 12 | 0.8 |
| 13 | 0.7 |
| 14 | 0.7 |
| 19 | 0.6 |

RP-HPLC: The RP-HPLC method utilizes a non-polar stationary phase and an aqueous moderately polar mobile phase. The HPLC is equipped with UV detection at 214 nm.

As shown in Table 7, RP-HPLC main peak percent purity decreases significantly as a function of temperature; however, formulation factors do not significantly impact the stability profile. Additionally, the predicted purity values approach 95% after 2 years storage at 5° C., indicating robustness across the formulation space at the nominal condition.

TABLE 7

Main peak purity (%) by RP-HPLC.

| Formulation | Condition | Peak Purity (%) Time (weeks) | | | |
|---|---|---|---|---|---|
| No. | (° C.) | 0 | 2 | 4 | 8 |
| 1 | 30 | 95.1 | 95.5 | 94.7 | 93.1 |
| | 40 | | 94.0 | 90.6 | 87.4 |
| | 5 | | — | 96.1 | 96.2 |
| 2 | 30 | 95.3 | 95.9 | 94.8 | 93.9 |
| | 40 | | 94.4 | 90.9 | 87.9 |
| | 5 | | — | 95.9 | 96.1 |
| 3 | 30 | 95.5 | 95.7 | 94.7 | 94.1 |
| | 40 | | 94.8 | 90.8 | 87.6 |
| | 5 | | — | 96.0 | 96.4 |

TABLE 7-continued

Main peak purity (%) by RP-HPLC.

| Formulation No. | Condition (° C.) | Peak Purity (%) Time (weeks) 0 | 2 | 4 | 8 |
|---|---|---|---|---|---|
| 4 | 30 | 95.6 | 95.6 | 94.6 | 94.1 |
| | 40 | | 94.8 | 91.4 | 88.5 |
| | 5 | | — | 96.2 | 96.3 |
| 5 | 30 | 95.3 | 95.5 | 94.6 | 93.8 |
| | 40 | | 94.3 | 91.1 | 88.2 |
| | 5 | | — | 96.5 | 96.3 |
| 6 | 30 | 94.4 | 95.3 | 94.5 | 93.8 |
| | 40 | | 94.1 | 90.6 | 87.3 |
| | 5 | | — | 95.8 | 96.0 |
| 7 | 30 | 95.4 | 95.9 | 94.7 | 94.3 |
| | 40 | | 94.1 | 90.8 | 87.9 |
| | 5 | | — | 96.0 | 96.3 |
| 8 | 30 | 95.1 | 95.5 | 94.4 | 94.1 |
| | 40 | | 94.4 | 91.1 | 88.2 |
| | 5 | | — | 95.8 | 96.3 |
| 9 | 30 | 95.5 | 95.6 | 94.4 | 93.5 |
| | 40 | | 94.1 | 90.7 | 87.5 |
| | 5 | | — | 95.7 | 96.1 |
| 10 | 30 | 94.5 | 95.7 | 94.9 | 94.0 |
| | 40 | | 94.8 | 91.3 | 87.7 |
| | 5 | | — | 96.4 | 96.4 |
| 11 | 30 | 94.7 | 95.6 | 94.7 | 94.0 |
| | 40 | | 94.2 | 91.0 | 87.7 |
| | 5 | | — | 95.7 | 96.0 |
| 12 | 30 | 93.6 | 95.5 | 94.6 | 93.8 |
| | 40 | | 94.3 | 90.7 | 87.5 |
| | 5 | | — | 95.9 | 96.2 |
| 13 | 30 | 94.3 | 95.5 | 94.7 | 93.9 |
| | 40 | | 94.4 | 91.2 | 88.2 |
| | 5 | | — | 96.3 | 95.3 |
| 14 | 30 | 94.2 | 95.5 | 95.0 | 94.0 |
| | 40 | | 94.6 | 91.4 | 88.7 |
| | 5 | | — | 95.9 | 96.6 |
| 19 | 30 | 95.2 | 95.5 | 94.6 | 94.1 |
| | 40 | | 94.2 | 91.6 | 88.5 |
| | 5 | | — | 96.2 | 96.0 |

The effects of the formulation factors on predicted values of RP-HPLC at the 5° C. condition after 24 months plus 1 month at 30° C. can be seen in Table 8, which shows that none of the study variables had a significant impact on main peak purity.

TABLE 8

RP-HPLC percent main peak purity (5%) predictions after 24 months storage at 5° C. plus 1 month at 30° C.

| Formulation No. | Main Peak Purity (%) |
|---|---|
| 1 | 94.6 |
| 2 | 94.9 |
| 3 | 95.1 |
| 4 | 95.2 |
| 5 | 94.9 |
| 6 | 93.9 |
| 7 | 95.0 |
| 8 | 94.6 |
| 9 | 94.6 |
| 10 | 94.6 |
| 11 | 94.3 |
| 12 | 93.5 |
| 13 | 94.0 |
| 14 | 94.2 |
| 19 | 94.8 |

Table 9 shows that total impurities by RP-HPLC increase with higher temperatures resulting in a more rapid rate of degradation.

TABLE 9

Total impurities by RP-HPLC.

| Formulation No. | Condition (° C.) | Time (weeks) 0 | 2 | 4 | 8 |
|---|---|---|---|---|---|
| 1 | 30 | 4.9 | 4.5 | 5.3 | 6.9 |
| | 40 | | 6 | 9.4 | 12.6 |
| | 5 | | — | 3.9 | 3.8 |
| 2 | 30 | 4.7 | 4.1 | 5.2 | 6.1 |
| | 40 | | 5.6 | 9.1 | 12.1 |
| | 5 | | — | 4.1 | 3.9 |
| 3 | 30 | 4.5 | 4.3 | 5.3 | 5.9 |
| | 40 | | 5.2 | 9.2 | 12.4 |
| | 5 | | | 4.0 | 3.6 |
| 4 | 30 | 4.4 | 4.4 | 5.4 | 5.9 |
| | 40 | | 5.2 | 8.6 | 11.5 |
| | 5 | | — | 3.8 | 3.7 |
| 5 | 30 | 4.7 | 4.5 | 5.4 | 6.2 |
| | 40 | | 5.7 | 8.9 | 11.8 |
| | 5 | | — | 3.5 | 3.7 |
| 6 | 30 | 5.6 | 4.7 | 5.5 | 6.2 |
| | 40 | | 5.9 | 9.4 | 12.7 |
| | 5 | | — | 4.2 | 4.0 |
| 7 | 30 | 4.6 | 4.1 | 5.3 | 5.7 |
| | 40 | | 5.9 | 9.2 | 12.1 |
| | 5 | | — | 4.0 | 3.7 |
| 8 | 30 | 4.9 | 4.5 | 5.6 | 5.9 |
| | 40 | | 5.6 | 8.9 | 11.8 |
| | 5 | | — | 4.2 | 3.7 |
| 9 | 30 | 4.5 | 4.4 | 5.6 | 6.5 |
| | 40 | | 5.9 | 9.3 | 12.5 |
| | 5 | | — | 4.3 | 3.9 |
| 10 | 30 | 5.5 | 4.3 | 5.1 | 6.0 |
| | 40 | | 5.2 | 8.7 | 12.3 |
| | 5 | | | 3.6 | 3.6 |
| 11 | 30 | 5.3 | 4.4 | 5.3 | 6.0 |
| | 40 | | 5.8 | 9.0 | 12.3 |
| | 5 | | — | 4.3 | 4.0 |
| 12 | 30 | 6.4 | 4.5 | 5.4 | 6.2 |
| | 40 | | 5.7 | 9.3 | 12.5 |
| | 5 | | — | 4.1 | 3.8 |
| 13 | 30 | 5.7 | 4.5 | 5.3 | 6.1 |
| | 40 | | 5.6 | 8.8 | 11.8 |
| | 5 | | — | 3.7 | 4.7 |
| 14 | 30 | 5.8 | 4.5 | 5.0 | 6.0 |
| | 40 | | 5.4 | 8.6 | 11.3 |
| | 5 | | — | 4.1 | 3.4 |
| 19 | 30 | 4.8 | 4.5 | 5.4 | 5.9 |
| | 40 | | 5.8 | 8.4 | 11.5 |
| | 5 | | — | 3.8 | 4.0 |

The effects of the formulation factors on predicted values of total impurities by RP-HPLC at 24 months, stored at 5° C. plus 1 month at 30° C. can be seen in Table 10, which shows that the overall the impact of study variables is not significant.

TABLE 10

RP-HPLC percent total impurities predicted values after 24 months.

| Formulation No. | Percent Total Impurities (%) |
|---|---|
| 1 | 5.4 |
| 2 | 5.1 |
| 3 | 4.9 |
| 4 | 4.8 |
| 5 | 5.1 |
| 6 | 6.1 |
| 7 | 5.0 |
| 8 | 5.4 |
| 9 | 5.4 |
| 10 | 5.4 |
| 11 | 5.7 |

TABLE 10-continued

| RP-HPLC percent total impurities predicted values after 24 months. | |
|---|---|
| Formulation No. | Percent Total Impurities (%) |
| 12 | 6.5 |
| 13 | 6.0 |
| 14 | 5.8 |
| 19 | 5.2 |

Physical stability and LCMS: physical appearance and visible particulates data are determined by visual inspection. There are no visible particulates reported at any time point/storage condition. In addition, the solutions remain clear and colorless until the 8-week time point at the 40° C. condition. Formulations 3, 8, 9, 15, 16, and 17 appear slightly amber as compared to the control (WFI) vial. Formulations 9 and 17 undergo LCMS analysis, and Formulation 19 further undergoes analysis as a comparison since it is clear and colorless. The matrices of formulations that experienced a color change are presented in Table 11.

TABLE 11

Matrices of formulations that changed color.

| Formulation No. | Buffer | pH | Incretin Analog (mg/mL) | Preservative | Tonicity Agent |
|---|---|---|---|---|---|
| 3 | Tris | 7.5 | 10 | m-cresol | glycerin |
| 8 | Tris | 7.5 | 10 | phenol | glycerin |
| 9 | Tris | 7.5 | 10 | m-cresol | mannitol |
| 15 | $PO_4$ | 7 | 6 | m-cresol | mannitol |
| 17 | $PO_4$ | 8 | 6 | phenol | mannitol |
| 16 | $PO_4$ | 8 | 6 | m-cresol | mannitol |

Formulations 9 and 19 are further compared as they share the same pH, buffer and tonicity modifier; however, formulation 9 includes m-cresol and formulation 19 includes no preservative. After 8 weeks of storage at 40° C., there are no significant differences in Total Ion Chromatograms (TICs) species identified between the formulations. LCMS analysis shows clipping at S8, isomerization and/or clipping at S32, clipping at Aib2, and a Y1 modification. Although the degradation pathways appear similar between the two formulations, formulation 9 shows a relatively higher levels of these modifications. Given that the difference between these formulations is the presence of m-cresol in formulation 9, the color change in formulation 9 may result from preservative degradation.

Conclusion: all formulations show similar stability profiles. Statistical analysis shows no significant impact on chemical stability resulting from the study variables. Therefore, there are no interactions between excipients, preservatives and incretin analog concentrations. In fact, incretin analog concentrations from 2 mg/mL to 10 mg/mL do not impact stability. These data indicate that m-cresol and phenol are preservatives for the incretin analog. The stability profile of formulation 19 (no preservative) is similar to all others. Predicted shelf-life for the main study arms and the non-preserved arm shows chemical stability out to 24 months at 5° C. plus 1 month at 30° C. The physical stability differences noted for some of the preserved formulations appears to be related to the stability of the preservative as opposed to a specific degradation pathway of the incretin analog. The data herein show that a non-preserved or a preserved solution formulation having an incretin analog from 2 to 10 mg/mL is feasible, utilizing either propylene glycol, glycerol or mannitol. Moreover, the data show no significant advantage of tonicity agent or preservative selection, with respect to shelf life.

Example 3: In-Use Stability Studies on Optimized, Prototype Formulations

Optimization: the optimization studies determine chemical and physical stability over time at nominal, accelerated and stressed conditions. Here, buffer and pH are optimized based upon the Examples above, with TRIS buffer at 10 mM and pH at 7.5 selected. As in the Examples above, the optimization here includes three tonicity modifiers: propylene glycol, glycerin and mannitol. A vial presentation is selected for optimization, and a syringe presentation is included to study incretin analog compatibility with a prefilled syringe. Table 12 describes the prototype formulation optimization parameters with an incretin analog of SEQ ID NO:1 or a pharmaceutically acceptable salt thereof.

TABLE 11

Prototype formulation optimization parameters.

| Prototype Formulation No. | Tonicity Modifier | Tonicity Concentration (mg/mL) | Primary Package | Incretin Analog Concentration (mg/mL) |
|---|---|---|---|---|
| P1 | propylene glycol | 20.1 | vial | 6 |
| P2 | mannitol | 48.1 | vial | 6 |
| P3 | glycerin | 24.3 | vial | 6 |
| P4 | glycerin | 24.3 | syringe | 6 |

NOTE:
all samples are prepared in a 10 mM TRIS buffer at pH 7.5 at 25° C.

Prototype formulation stability testing: samples are placed on stability for up to 6 months and tested according to Table 13. The main analytical assays are RP-HPLC and SEC. An AEX method also is used as an orthogonal characterization test.

TABLE 12

Prototype formulation stability testing design.

| Test | Method | Storage | Initial | 1 | 2 | 3 | 6 |
|---|---|---|---|---|---|---|---|
| Appearance/ Visible Particulates | Visual | 5° C. | X | X | X | X | ○ |
| | | 25° C. | | | X | X | ○ |
| | | 30° C. | | X | | | |
| | | 35° C. | | X | X | X | |
| Particulate Matter | HIAC and MFI* | 5° C. | X | X | X | X | ○ |
| | | 25° C. | | | X | X | ○ |
| | | 30° C. | | X | | | |
| | | 35° C. | | X | X | X | |
| Quantity/ Purity | RP-HPLC | 5° C. | X | X | X | X | ○ |
| | | 25° C. | | | X | X | ○ |
| | | 30° C. | | X | | | |
| | | 35° C. | | X | X | X | |
| Purity | SEC | 5° C. | X | X | X | X | ○ |
| | | 25° C. | | | X | X | ○ |
| | | 30° C. | | X | | | |
| | | 35° C. | | X | X | X | |
| Purity | AEX | 5° C. | X | X | X | X | ○ |
| | | 25° C. | | | X | X | ○ |
| | | 30° C. | | X | | | |
| | | 35° C. | | X | X | X | |
| pH | pH meter | 5° C. | X | X | X | X | ○ |
| | | 25° C. | | | X | X | ○ |
| | | 30° C. | | X | | | |
| | | 35° C. | | X | X | X | |

TABLE 12-continued

Prototype formulation stability testing design.

| Test | Method | Storage | Initial | 1 | 2 | 3 | 6 |
|---|---|---|---|---|---|---|---|
| Bioassay | Cell based | 5° C. | X | | | | X |
| | | 25° C. | | | | | |
| | | 30° C. | | | | | |
| | | 35° C. | | | | | |
| Break | Instron | 5° C. | X | | | | |
| Loose/Glide | | 25° C. | | X | X | X | ○ |
| Force | | 30° C. | | | | | |
| | | 35° C. | | | | | |

*MFI is tested for the syringe presentation only.

CSD, ISTA 3A and photo degradation testing: a solution matrix is used and is determined based on the Examples above. An exemplary drug product unit formulation herein is summarized in Table 14.

TABLE 14

Drug product unit formula.

| Ingredient | Quantity per Vial (mg) | Quantity per mL (mg) |
|---|---|---|
| Incretin Analog (SEQ ID NO: 1) | 12 | 6 |
| Tris base | 2.42 | 1.21 |
| Mannitol | 96 | 48 |
| Water for Injection | q.s. to 2.0 mL | q.s. to 1.0 mL |
| Hydrochloric Acid Solution | pH adjustment | pH adjustment |

The incretin analog (SEQ ID NO:1) tetrasodium salt is tested for shear and vibrational sensitivity using a capillary shear device and the ISTA 3A testing method. Photostability is tested at this stage as well, to support manufacturing and packaging operations. The capillary shear device is developed to model shear similar to that which may be caused by manufacturing unit operations (mixing, pumping, filling, etc.). The ISTA 3A testing is a simulated shipping study designed to mimic vibrational stress during shipping. Both methods are considered worst case for either type of physical stress they are designed to model. Both study methods follow standard testing protocols. Photostability testing is carried out as follows: samples are loaded into the photostability chamber and exposed to one of three levels of intensity and type (both UV and Visible) according to ICH guidelines: 0%, 20% and 100% of ICH recommended intensity. Table 15 outlines the design and testing plan for these studies.

TABLE 15

Photostability, CSD and ISTA 3A design.

| Samples | Description | Analytical Properties | Methods |
|---|---|---|---|
| CSD control | non-stressed CSD Control | appearance & visible | visual |
| stainless steel | pumped through stainless steel capillary | particulates | |
| stainless steel/air | pumped through stainless steel capillary w/air gap | sub visible particulates | HIAC |
| shipping control | non-stressed shipping control | monomer purity | SEC |
| ISTA 3A | shipping stress | main peak purity | RP-HPLC |
| photo dark control | non-exposed photostability control | charge heterogeneity | AEX |
| photo, 20% ICH | UV/visible light exposure | pH | USP |
| photo, 100% ICH | UV/visible light exposure | | |

In these studies, bioassay analysis (data not shown) is carried out on prototypes P1 and P2 at time 0 and also is carried out on P2 at the 6-month time point only. The bioassay results show no significant difference between tested samples. Overall, the studies show a robust chemical and physical stability profile, with temperature playing the largest role in degradation.

RP-HPLC results: there is essentially no change at 5° C., with main peak purity decreasing as a function of temperature. Differences between formulations at the stressed and accelerated conditions are within method variability.

TABLE 16

RP-HPLC main peak results, prototype study.

| Formulation No. | Temp. (° C.) | Time (weeks) 0 | 1 | 2 | 3 | 6 |
|---|---|---|---|---|---|---|
| P1 | 5 | 95.9 | 95.9 | 96.1 | 95.7 | 96.0 |
| | 25 | 95.9 | — | 95.1 | 93.5 | 91.9 |
| | 30 | 95.9 | 94.7 | — | — | — |
| | 35 | 95.9 | 93.1 | 91.3 | 87.6 | |
| P2 | 5 | 95.9 | 95.9 | 96.1 | 95.8 | 96.1 |
| | 25 | 95.9 | — | 94.9 | 93.3 | 90.6 |
| | 30 | 95.9 | 94.6 | — | — | — |
| | 35 | 95.9 | 93.0 | 89.7 | 87.2 | — |
| P3 | 5 | 95.9 | 95.7 | 96.2 | 95.5 | 96.0 |
| | 25 | 95.9 | — | 95.1 | 93.3 | 92.2 |
| | 30 | 95.9 | 94.3 | — | — | — |
| | 35 | 95.9 | 93.3 | 91.4 | 87.7 | — |
| P4 | 5 | 96.0 | 95.7 | 96.3 | 95.5 | 96.2 |
| | 25 | 96.0 | — | 94.8 | 93.4 | 92.0 |
| | 30 | 96.0 | 94.6 | — | — | — |
| | 35 | 96.0 | 93.5 | 91.4 | 87.7 | — |

TABLE 17

RP-HPLC total impurities results, prototype study.

| Formulation No. | Temp. (° C.) | Time (months) 0 | 1 | 2 | 3 | 6 |
|---|---|---|---|---|---|---|
| P1 | 5 | 4.1 | 4.1 | 3.9 | 4.3 | 4.0 |
| | 25 | 4.1 | — | 4.9 | 6.5 | 8.1 |
| | 30 | 4.1 | 5.3 | — | — | — |
| | 35 | 4.1 | 6.9 | 8.7 | 12.4 | — |
| P2 | 5 | 4.1 | 4.1 | 3.9 | 4.2 | 3.9 |
| | 25 | 4.1 | — | 5.1 | 6.7 | 9.4 |
| | 30 | 4.1 | 5.4 | — | — | — |
| | 35 | 4.1 | 7.0 | 10.3 | 12.8 | — |
| P3 | 5 | 4.1 | 4.3 | 3.8 | 4.5 | 4.0 |
| | 25 | 4.1 | — | 4.9 | 6.7 | 7.8 |
| | 30 | 4.1 | 5.7 | — | — | — |
| | 35 | 4.1 | 6.7 | 8.6 | 12.3 | — |
| P4 | 5 | 4.0 | 4.3 | 3.7 | 4.5 | 3.8 |
| | 25 | 4.0 | — | 5.2 | 6.6 | 8.0 |
| | 30 | 4.0 | 5.4 | — | — | — |
| | 35 | 4.0 | 6.5 | 8.6 | 12.3 | — |

SEC results: SEC results at the 5° C. condition show no significant differences or discernable trends at this condition. Monomer purity results at the accelerated and stressed conditions decrease at the 2- and 3-month time points. Similarly, total aggregates increase drastically at accelerated and stressed conditions. The monomer purity results for all conditions at the accelerated and stressed conditions are within 1% of each other, which is close to the method variability.

TABLE 18

SEC % monomer results, prototype study.

| Formulation No. | Temp. (° C.) | Time (weeks) 0 | 1 | 2 | 3 | 6 |
|---|---|---|---|---|---|---|
| P1 | 5 | 98.8 | 98.4 | 98.7 | 98.1 | 98.1 |
| | 25 | 98.8 | — | 98.5 | 98.1 | 97.7 |
| | 30 | 98.8 | 98.1 | — | — | — |
| | 35 | 98.8 | 98.5 | 95.8 | 94.5 | — |
| P2 | 5 | 98.7 | 98.4 | 98.5 | 98.1 | 98.1 |
| | 25 | 98.7 | — | 98.4 | 98.0 | 97.3 |
| | 30 | 98.7 | 98.4 | — | — | — |
| | 35 | 98.7 | 98.4 | 95.8 | 93.9 | — |
| P3 | 5 | 98.7 | 98.3 | 98.4 | 98.2 | 98.2 |
| | 25 | 98.7 | — | 98.3 | 98.1 | 97.8 |
| | 30 | 98.7 | 98.5 | — | — | — |
| | 35 | 98.7 | 98.6 | 96.2 | 94.7 | |
| P4 | 5 | 98.6 | 98.4 | 98.7 | 98.2 | 98.2 |
| | 25 | 98.6 | — | 98.6 | 98.0 | 97.7 |
| | 30 | 98.6 | 98.4 | — | — | — |
| | 35 | 98.6 | 98.2 | 96.0 | 94.6 | — |

TABLE 19

SEC % total aggregates results, prototype study.

| Formulation No. | Temp. (° C.) | Time (months) 0 | 1 | 2 | 3 | 6 |
|---|---|---|---|---|---|---|
| P1 | 5 | 0.6 | 0.7 | 0.6 | 0.7 | 0.7 |
| | 25 | 0.6 | — | 0.7 | 0.8 | 1.0 |
| | 30 | 0.6 | 0.8 | — | — | — |
| | 35 | 0.6 | 0.8 | 3.3 | 4.4 | — |
| P2 | 5 | 0.6 | 0.7 | 0.6 | 0.7 | 0.8 |
| | 25 | 0.6 | — | 0.7 | 0.9 | 1.5 |
| | 30 | 0.6 | 0.8 | — | — | — |
| | 35 | 0.6 | 0.8 | 3.3 | 4.9 | — |
| P3 | 5 | 0.6 | 0.7 | 0.6 | 0.7 | 0.7 |
| | 25 | 0.6 | — | 0.8 | 0.8 | 1.0 |
| | 30 | 0.6 | 0.7 | — | — | — |
| | 35 | 0.6 | 0.8 | 2.9 | 4.1 | — |
| P4 | 5 | 0.6 | 0.7 | 0.6 | 0.7 | 0.7 |
| | 25 | 0.6 | — | 0.7 | 0.9 | 1.0 |
| | 30 | 0.6 | 0.7 | — | — | — |
| | 35 | 0.6 | 0.8 | 3.0 | 4.1 | — |

AEX results: AEX results at the 5° C. condition show an increase in acidic variants of about 2% after 6 months, although there is some inherent variation in the data. The acidic variants increase overall as a function of temperature, appearing to level off at about 7%.

TABLE 20

AEX % main peak results, prototype study.

| Formulation No. | Temp. (° C.) | Time (weeks) 0 | 1 | 2 | 3 | 6 |
|---|---|---|---|---|---|---|
| P1 | 5 | 97.6 | 96.4 | 96.6 | 97.2 | 95.6 |
| | 25 | 97.6 | — | 94.7 | 95.5 | 91.2 |
| | 30 | 97.6 | 94.4 | — | — | — |
| | 35 | 97.6 | 93.7 | 91.8 | 92.7 | — |
| P2 | 5 | 97.7 | 96.7 | 96.3 | 97.0 | 95.5 |
| | 25 | 97.7 | — | 94.4 | 95.8 | 90.7 |
| | 30 | 97.7 | 94.2 | — | — | — |
| | 35 | 97.7 | 93.3 | 91.1 | 91.5 | — |
| P3 | 5 | 97.6 | 96.3 | 96.6 | 97.2 | 95.4 |
| | 25 | 97.6 | — | 94.8 | 95.5 | 91.3 |
| | 30 | 97.6 | 94.6 | — | — | — |
| | 35 | 97.6 | 93.7 | 91.7 | 92.6 | — |

TABLE 20-continued

AEX % main peak results, prototype study.

| Formulation No. | Temp. (° C.) | Time (weeks) 0 | 1 | 2 | 3 | 6 |
|---|---|---|---|---|---|---|
| P4 | 5 | 97.5 | 96.6 | 96.5 | 97.2 | 95.5 |
| | 25 | 97.5 | — | 94.6 | 95.5 | 91.3 |
| | 30 | 97.5 | 94.9 | — | — | — |
| | 35 | 97.5 | 93.9 | 91.7 | 92.7 | — |

TABLE 21

AEX % total acidic variants, prototype study.

| Formulation No. | Temp. (° C.) | Time (weeks) 0 | 1 | 2 | 3 | 6 |
|---|---|---|---|---|---|---|
| P1 | 5 | 1.2 | 2.4 | 2.3 | 1.6 | 3.2 |
| | 25 | 1.2 | — | 4.2 | 3.4 | 7.5 |
| | 30 | 1.2 | 4.3 | — | — | — |
| | 35 | 1.2 | 5.1 | 7.0 | 6.1 | — |
| P2 | 5 | 1.2 | 2.2 | 2.5 | 1.7 | 3.3 |
| | 25 | 1.2 | — | 4.4 | 3.1 | 8.0 |
| | 30 | 1.2 | 4.5 | — | — | — |
| | 35 | 1.2 | 5.4 | 7.5 | 7.2 | — |
| P3 | 5 | 1.2 | 2.4 | 2.2 | 1.6 | 3.3 |
| | 25 | 1.2 | — | 4.0 | 3.3 | 7.4 |
| | 30 | 1.2 | 4.1 | — | — | — |
| | 35 | 1.2 | 5.0 | 7.0 | 6.1 | — |
| P4 | 5 | 1.3 | 2.2 | 2.3 | 1.6 | 3.3 |
| | 25 | 1.3 | — | 4.2 | 3.4 | 7.4 |
| | 30 | 1.3 | 3.9 | — | — | — |
| | 35 | 1.3 | 4.9 | 7.0 | 6.1 | — |

Subvisible particulate matter results: particulate matter data over the entire study shows no significant differences as a function of tonicity modifier. Particulate matter≥10 μm and ≥25 μm are well below specification limits. Table 22 shows particulate matter≥2 μm by HIAC. Cumulative counts per mL are low across all conditions but are naturally higher in the syringe presentation due to the presence of silicone oil not being present in the vial presentations. Particulate matter data by MFI collected on the syringe presentation (data not shown) were highly variable and showed no clear trends. However, the counts overall showed no interaction with the increased silicone oil present in the syringe presentation.

TABLE 22

Subvisible particulate matter ≥2 μm by light obscuration method, prototype study.

| Formulation No. | Temp. (° C.) | Time (months) 0 | 1 | 2 | 3 | 6 |
|---|---|---|---|---|---|---|
| P1 | 5 | 330 | 664 | 254 | 207 | 115 |
| | 25 | 330 | — | 162 | 80 | 57 |
| | 30 | 330 | 181 | — | — | — |
| | 35 | 330 | 200 | 44 | 183 | |
| P2 | 5 | 256 | 1062 | 74 | 138 | 432 |
| | 25 | 256 | — | 96 | 125 | 151 |
| | 30 | 256 | 169 | — | — | — |
| | 35 | 256 | 419 | 42 | 72 | — |
| P3 | 5 | 103 | 1369 | 66 | 106 | 308 |
| | 25 | 103 | — | 50 | 114 | 68 |
| | 30 | 103 | 443 | — | — | — |
| | 35 | 103 | 157 | 39 | 23 | — |

TABLE 22-continued

Subvisible particulate matter ≥2 μm by light obscuration method, prototype study.

| Formulation No. | Temp. (° C.) | Time (months) 0 | 1 | 2 | 3 | 6 |
|---|---|---|---|---|---|---|
| P4 | 5 | 983 | 2156 | 1211 | 1483 | 1801 |
| | 25 | 983 | — | 1281 | 1643 | 1937 |
| | 30 | 983 | 1287 | — | — | — |
| | 35 | 983 | 1638 | 1856 | 1397 | — |

Appearance, pH and visible particulates results: appearance results (data not shown) across all conditions is clear and colorless. No visible particulates are reported throughout the study. pH results are summarized in Table 23 and show variable results and no clear trending. All pH values are within 0.2 pH units of the target.

TABLE 23 pH results, prototype study.

| Formulation No. | Temp. (° C.) | Time (months) 0 | 1 | 2 | 3 | 6 |
|---|---|---|---|---|---|---|
| P1 | 5 | 7.48 | 7.36 | 7.42 | 7.44 | 7.43 |
| | 25 | 7.48 | — | 7.45 | 7.41 | 7.46 |
| | 30 | 7.48 | 7.35 | — | — | — |
| | 35 | 7.48 | 7.45 | 7.45 | 7.41 | — |
| P2 | 5 | 7.47 | 7.38 | 7.40 | 7.40 | 7.48 |
| | 25 | 7.47 | — | 7.44 | 7.40 | 7.45 |
| | 30 | 7.47 | 7.43 | — | — | — |
| | 35 | 7.47 | 7.44 | 7.40 | 7.42 | — |
| P3 | 5 | 7.40 | 7.30 | 7.33 | 7.31 | 7.37 |
| | 25 | 7.40 | — | 7.33 | 7.33 | 7.38 |
| | 30 | 7.40 | 7.36 | — | — | — |
| | 35 | 7.40 | 7.32 | 7.35 | 7.33 | — |
| P4 | 5 | 7.46 | 7.38 | 7.37 | 7.30 | 7.35 |
| | 25 | 7.46 | — | 7.40 | 7.29 | 7.36 |
| | 30 | 7.46 | 7.33 | — | — | — |
| | 35 | 7.46 | 7.39 | 7.40 | 7.30 | — |

Break-loose and glide-force (BLGF) results: Prototype formulation P4 is tested for BLGF. Data are collected at the 25° C. condition only. Table 24 shows that BLGF data stay well below their respective functionality limits, suggesting good compatibility with this system. Functionality limits are established break-loose and glide-force maximum operating limits for the Irma autoinjector and are 13.6 N and 9.5 N, respectively.

TABLE 24

BLGF results, prototype study.

| Syringe Force Testing | Time (months) 0 | 1 | 2 | 3 | 6 |
|---|---|---|---|---|---|
| Reported Break Loose Force (N) | 3.9 | 3.8 | 3.6 | 3.7 | 4.1 |
| Reported Peak Glide Force (N) | 2.5 | 3.1 | 2.7 | 2.5 | 3.0 |

Chemical stability results: RP-HPLC and SEC results show a slight difference between the 100% photo stressed sample and its control sample. The change in purity is about 0.8%. The other conditions are within the variability of the method. Table 26 shows that the SEC results show a higher level of aggregates for the 100% photo stressed sample but otherwise results for aggregates are low overall. AEX results show no significant change resulting from the stressed conditions.

TABLE 26

| CSD/Shipping/Photo Studies, % purity by SEC. | | | | | | | | | | | |
|---|---|---|---|---|---|---|---|---|---|---|---|
| Sample ID | SEC % Mon. | SEC % Agg. | SEC % PM | RP Quant. (mg/mL) | RP % MP | RP % LURS | RP % TRS | AEX % AV | AEX % BV | AEX % MP | pH |
| CSD SS/Air | 97.4 | 0.5 | 2.1 | 6.3 | 96.0 | 0.9 | 4.0 | 2.7 | 1.3 | 96.1 | NR |
| CSD SS | 97.4 | 0.5 | 2.1 | 6.2 | 96.2 | 0.9 | 3.8 | 2.6 | 1.2 | 96.2 | NR |
| CSD Control | 97.4 | 0.5 | 2.1 | 6.2 | 96.2 | 0.9 | 3.8 | 2.6 | 1.2 | 96.2 | NR |
| Photo, Dark Control | 98.5 | 0.6 | 0.9 | 6.1 | 95.9 | 1.2 | 4.1 | 2.2 | 1.3 | 96.5 | 7.22 |
| Photo, Exposed 100% | 97.7 | 1.2 | 1.1 | 6.0 | 95.4 | 1.2 | 4.6 | 2.2 | 1.1 | 96.7 | 7.15 |
| Photo, Exposed 20% | 98.5 | 0.7 | 0.9 | 6.1 | 95.9 | 1.2 | 4.1 | 1.4 | 1.2 | 97.4 | 7.18 |
| Ship., Control | 98.6 | 0.6 | 0.8 | 6.1 | 96.0 | 1.2 | 4.0 | 1.8 | 1.3 | 97.0 | 7.14 |
| Ship., Exposed | 98.4 | 0.6 | 1.0 | 6.1 | 96.2 | 1.0 | 3.8 | 1.9 | 1.3 | 96.8 | 7.15 |

Physical stability results: particulate matter by HIAC results are summarized in Tables 27 and 28. These data show no major differences between control and stressed samples. Visible particulates (data not shown) are reported for the shipping and photostability stressed samples; however, those results are shown to be false positives.

TABLE 27

| CSD/Shipping/Photo Studies, particulate matter by light obscuration method. | | | | |
|---|---|---|---|---|
| Sample ID | ≥2 μm | ≥5 μm | ≥10 μm | ≥25 μm |
| Shipping, Control | 102 | 7 | 1 | 0 |
| Shipping, Exposed | 158 | 11 | 0 | 0 |
| Photo, Dark Control | 129 | 10 | 1 | 0 |
| Photo, Exposed 20% | 152 | 9 | 0 | 0 |
| Photo, Exposed 100% | 259 | 27 | 3 | 1 |
| SS/Air | 326 | 29 | 3 | 0 |
| SS | 266 | 25 | 1 | 0 |
| CSD Control | 31 | 10 | 3 | 0 |

The studies herein show acceptable physical and chemical stability of the incretin analog formulations out to 6 months at nominal, accelerated and stressed conditions. Incretin analog degradation is primarily a function of temperature. There are no significant differences between any of the 3 prototypes (note: P3 and P4 are identical compositions except that P4 is filled into syringes instead of vials). The syringe presentation shows acceptable BLGF results as well, indicating compatibility with a third-generation platform syringe system. In view thereof, P2 is a leading formulation for clinical studies.

After exposures to shear and vibrational stress via the CSD and shipping studies, P2 shows no significant differences between stressed samples and non-stressed (control) samples. Additionally, the photostability study at 20% ICH conditions shows no major difference compared to dark control. However, small differences compared to the dark control are observed after exposure to 100% of the ICH conditions.

A solution composition is selected based on these data that includes 4.8% mannitol and 10 mM tris buffer, at pH 7.5. The incretin analog concentration is fixed at 6 mg/mL with a fill volume of 2 mL to cover a proposed dose range (e.g., about 0.5 mg to about 12 mg). The container/closure size for clinical studies is a 2 mL Schott vial with a corresponding serum stopper and seal (BT5973/VS5558/AZ5450). Statistical analysis of P2 predicts robust stability after 2 years of storage, including a 30-day, 30° C. in-use period.

Example 4: Stability Studies on Prototype Formulation P2 Under Varying Levels of Incretin Analog Peptide Concentration and pH The purpose of this Design of Experiments (DOE) study is to define and confirm the robustness of the prototype P2 formulation under varying levels of incretin analog peptide concentration and pH conditions.

The solution matrix constituents are as follows: 10 mM Tris, 4.8% mannitol. The peptide concentration is examined at three concentration levels: 1, 18 and 30 mg/mL of SEQ ID NO:1 (tetrasodium salt). The pH effect is studied at 3 pH levels: 7, 7.5 and 8. To prepare solutions, the peptide is dissolved into a known quantity of the buffer matrix, concentration is measured using a UV/Vis spectrophotometer equipped with a variable path length extension, the target weight is calculated based on the assay result and density of the target formulation, and the required amount of buffer is added to achieve the final target weight. The primary packaging materials used are the commercial-image (Generation II) prefilled syringe barrel, coupled with the non-laminated (Generation II) stopper. Syringes are filled to a nominal volume of 0.5 mL. The formulations are shown below in Table 28.

TABLE 38

| Formulations | | | |
|---|---|---|---|
| Formulation # | Matrix | Incretin analog (SEQ ID NO: 1) Concentration (mg/mL) | pH |
| 1 | 10 mM Tris | 18 | 7.5 |
| 2 | 4.8% Mannitol | 30 | 7.5 |
| 3 | | 30 | 7 |
| 4 | | 30 | 7 |

TABLE 38-continued

| Formulations | | | |
|---|---|---|---|
| Formulation # | Matrix | Incretin analog (SEQ ID NO: 1) Concentration (mg/mL) | pH |
| 5 | | 18 | 8 |
| 6 | | 1 | 7 |
| 7 | | 30 | 8 |
| 8 | | 1 | 8 |
| 9 | | 1 | 7.5 |
| 10 | | 18 | 7.5 |

Stability-indicating analytical and characterization techniques selected to measure the chemical and physical stability of the formulations include size exclusion chromatography (SEC), reversed phase high performance liquid chromatography (RP-HPLC), Anion Exchange Chromatography (AEX), HIAC, Microflow Imaging technique (MFI) and visual appearance. Samples are stored at two temperature conditions (5° C. and 30° C.). The sampling schedule is outlined in Table 29, and data shown in Tables 30-32. Prediction plots out to 23 months at 5° C.+30 days at 30° C. are generated based on statistical analysis in order to predict degradation levels at the end of shelf-life.

TABLE 29

| Planned Sampling Schedule | | | | | | |
|---|---|---|---|---|---|---|
| Storage Condition | Time (Months) | | | | | |
| (° C.) | 0 | 0.5 | 1 | 2 | 3 | 6 |
| 5 | X | — | X | X | X | X |
| 30 | X | X | X | X | X | X |

TABLE 30

| Appearance, pH and Content | | | | | | | | |
|---|---|---|---|---|---|---|---|---|
| Formulation | Timepoint (Months) | Condition (° C.) | Visible Particles | Color | Clarity White Background | Clarity Black Background | Content mg/mL | Avg pH |
| 1 | 0 | 5 | Liquid | None | Colorless | Clear | Clear | 7.47 |
| 10 | 0 | 5 | Liquid | None | Colorless | Clear | Clear | 7.51 |
| 2 | 0 | 5 | Liquid | None | Colorless | Clear | Clear | 7.45 |
| 3 | 0 | 5 | Liquid | None | Colorless | Clear | Clear | 7.37 |
| 4 | 0 | 5 | Liquid | None | Colorless | Clear | Clear | 7.36 |
| 5 | 0 | 5 | Liquid | None | Colorless | Clear | Clear | 7.83 |
| 6 | 0 | 5 | Liquid | None | Colorless | Clear | Clear | 7.17 |
| 7 | 0 | 5 | Liquid | None | Colorless | Clear | Clear | 7.76 |
| 8 | 0 | 5 | Liquid | None | Colorless | Clear | Clear | 8.03 |
| 9 | 0 | 5 | Liquid | None | Colorless | Clear | Clear | 7.49 |
| 1 | 0 | 30 | Liquid | None | Colorless | Clear | Clear | 7.47 |
| 10 | 0 | 30 | Liquid | None | Colorless | Clear | Clear | 7.51 |
| 2 | 0 | 30 | Liquid | None | Colorless | Clear | Clear | 7.45 |
| 3 | 0 | 30 | Liquid | None | Colorless | Clear | Clear | 7.37 |
| 4 | 0 | 30 | Liquid | None | Colorless | Clear | Clear | 7.36 |
| 5 | 0 | 30 | Liquid | None | Colorless | Clear | Clear | 7.83 |
| 6 | 0 | 30 | Liquid | None | Colorless | Clear | Clear | 7.17 |
| 7 | 0 | 30 | Liquid | None | Colorless | Clear | Clear | 7.76 |
| 8 | 0 | 30 | Liquid | None | Colorless | Clear | Clear | 8.03 |
| 9 | 0 | 30 | Liquid | None | Colorless | Clear | Clear | 7.49 |
| 1 | 0.5 | 30 | Liquid | None | Colorless | Clear | Clear | 7.68 |
| 10 | 0.5 | 30 | Liquid | None | Colorless | Clear | Clear | 7.61 |
| 2 | 0.5 | 30 | Liquid | None | Colorless | Clear | Clear | 7.59 |
| 3 | 0.5 | 30 | Liquid | None | Colorless | Clear | Clear | 7.47 |
| 4 | 0.5 | 30 | Liquid | None | Colorless | Clear | Clear | 7.46 |
| 5 | 0.5 | 30 | Liquid | None | Colorless | Clear | Clear | 7.88 |
| 6 | 0.5 | 30 | Liquid | None | Colorless | Clear | Clear | 7.02 |
| 7 | 0.5 | 30 | Liquid | None | Colorless | Clear | Clear | 7.87 |
| 8 | 0.5 | 30 | Liquid | None | Colorless | Clear | Clear | 7.88 |
| 9 | 0.5 | 30 | Liquid | None | Colorless | Clear | Clear | 7.35 |
| 1 | 1 | 30 | Liquid | None | Colorless | Clear | Clear | 7.60 |
| 2 | 1 | 30 | Liquid | None | Colorless | Clear | Clear | 7.70 |
| 3 | 1 | 30 | Liquid | None | Colorless | Clear | Clear | 7.57 |
| 4 | 1 | 30 | Liquid | None | Colorless | Clear | Clear | 7.56 |
| 5 | 1 | 30 | Liquid | None | Colorless | Clear | Clear | 8.07 |
| 6 | 1 | 30 | Liquid | None | Colorless | Clear | Clear | 7.18 |
| 7 | 1 | 30 | Liquid | None | Colorless | Clear | Clear | 7.89 |
| 8 | 1 | 30 | Liquid | None | Colorless | Clear | Clear | 8.01 |
| 9 | 1 | 30 | Liquid | None | Colorless | Clear | Clear | 7.47 |
| 10 | 1 | 30 | Liquid | None | Colorless | Clear | Clear | 7.74 |
| 1 | 1 | 5 | Liquid | None | Colorless | Clear | Clear | 7.60 |
| 2 | 1 | 5 | Liquid | None | Colorless | Clear | Clear | 7.53 |
| 3 | 1 | 5 | Liquid | None | Colorless | Clear | Clear | 7.49 |
| 4 | 1 | 5 | Liquid | None | Colorless | Clear | Clear | 7.50 |
| 5 | 1 | 5 | Liquid | None | Colorless | Clear | Clear | 7.89 |
| 6 | 1 | 5 | Liquid | None | Colorless | Clear | Clear | 7.19 |
| 7 | 1 | 5 | Liquid | None | Colorless | Clear | Clear | 7.81 |
| 8 | 1 | 5 | Liquid | None | Colorless | Clear | Clear | 8.09 |
| 9 | 1 | 5 | Liquid | None | Colorless | Clear | Clear | 7.57 |
| 10 | 1 | 5 | Liquid | None | Colorless | Clear | Clear | 7.63 |

TABLE 30-continued

Appearance, pH and Content

| Formulation | Timepoint (Months) | Condition (° C.) | Visible Particles | Color | Clarity White Background | Clarity Black Background | Content mg/mL | Avg pH |
|---|---|---|---|---|---|---|---|---|
| 1 | 2 | 30 | Liquid | None | Colorless | Clear | Clear | 7.67 |
| 2 | 2 | 30 | Liquid | None | Colorless | Clear | Clear | 7.71 |
| 3 | 2 | 30 | Liquid | None | Colorless | Clear | Clear | 7.61 |
| 4 | 2 | 30 | Liquid | None | Colorless | Clear | Clear | 7.55 |
| 5 | 2 | 30 | Liquid | None | Colorless | Clear | Clear | 8.01 |
| 6 | 2 | 30 | Liquid | None | Colorless | Clear | Clear | 7.19 |
| 7 | 2 | 30 | Liquid | None | Colorless | Clear | Clear | 7.95 |
| 8 | 2 | 30 | Liquid | None | Colorless | Clear | Clear | 8.09 |
| 9 | 2 | 30 | Liquid | None | Colorless | Clear | Clear | 7.47 |
| 10 | 2 | 30 | Liquid | None | Colorless | Clear | Clear | 7.69 |
| 1 | 2 | 5 | Liquid | None | Colorless | Clear | Clear | 7.56 |
| 2 | 2 | 5 | Liquid | None | Colorless | Clear | Clear | 7.53 |
| 3 | 2 | 5 | Liquid | None | Colorless | Clear | Clear | 7.49 |
| 4 | 2 | 5 | Liquid | None | Colorless | Clear | Clear | 7.46 |
| 5 | 2 | 5 | Liquid | None | Colorless | Clear | Clear | 7.86 |
| 6 | 2 | 5 | Liquid | None | Colorless | Clear | Clear | 7.17 |
| 7 | 2 | 5 | Liquid | None | Colorless | Clear | Clear | 7.77 |
| 8 | 2 | 5 | Liquid | None | Colorless | Clear | Clear | 8.04 |
| 9 | 2 | 5 | Liquid | None | Colorless | Clear | Clear | 7.52 |
| 10 | 2 | 5 | Liquid | None | Colorless | Clear | Clear | 7.54 |
| 1 | 3 | 30 | Liquid | None | Colorless | Clear | Clear | 7.71 |
| 2 | 3 | 30 | Liquid | None | Colorless | Clear | Clear | 7.67 |
| 3 | 3 | 30 | Liquid | None | Colorless | Clear | Clear | 7.58 |
| 4 | 3 | 30 | Liquid | None | Colorless | Clear | Clear | 7.55 |
| 5 | 3 | 30 | Liquid | None | Colorless | Clear | Clear | 8.00 |
| 6 | 3 | 30 | Liquid | None | Colorless | Clear | Clear | 7.22 |
| 7 | 3 | 30 | Liquid | None | Colorless | Clear | Clear | 7.95 |

TABLE 31

RP-HPLC, SEC and AEX Results

| Formulation | Time Point (Months) | Condition (° C.) | RP-HPLC % Main Peak | RP-HPLC % LURS | RP-HPLC % Total Impurities | SEC % Monomer | SEC % Total Aggregates | SEC % Total Fragments | AEX % TAV | AEX % TBV | AEX % Main Peak |
|---|---|---|---|---|---|---|---|---|---|---|---|
| 1 | 0 | 5 | 97.0075 | 0.8071 | 2.9925 | 98.0555 | 0.3007 | 1.6438 | 0.9431 | 0.8726 | 98.1843 |
| 10 | 0 | 5 | 97.0222 | 0.7906 | 2.9778 | 98.1322 | 0.2946 | 1.5732 | 0.8602 | 0.8681 | 98.2718 |
| 2 | 0 | 5 | 97.0579 | 0.7927 | 2.9421 | 98.0652 | 0.3017 | 1.6331 | 0.9873 | 0.8763 | 98.1364 |
| 3 | 0 | 5 | 97.0086 | 0.8149 | 2.9914 | 98.0938 | 0.3004 | 1.6057 | 0.9251 | 0.8708 | 98.2040 |
| 4 | 0 | 5 | 97.0791 | 0.8085 | 2.9209 | 98.0894 | 0.2921 | 1.6185 | 0.8721 | 0.8753 | 98.2527 |
| 5 | 0 | 5 | 96.9528 | 0.7925 | 3.0472 | 98.1136 | 0.2960 | 1.5904 | 0.8359 | 0.8624 | 98.3017 |
| 6 | 0 | 5 | 97.0366 | 0.8108 | 2.9634 | 98.1143 | 0.2984 | 1.5873 | 0.7836 | 0.8730 | 98.3434 |
| 7 | 0 | 5 | 96.9816 | 0.7856 | 3.0184 | 98.1764 | 0.2726 | 1.5510 | 0.8663 | 0.8751 | 98.2586 |
| 8 | 0 | 5 | 96.8139 | 0.7921 | 3.1861 | 98.1565 | 0.3033 | 1.5402 | 0.8450 | 0.8630 | 98.2920 |
| 9 | 0 | 5 | 97.0271 | 0.7890 | 2.9729 | 98.0997 | 0.3187 | 1.5815 | 0.8139 | 0.8742 | 98.3119 |
| 1 | 0 | 30 | 97.0075 | 0.8071 | 2.9925 | 98.0555 | 0.3007 | 1.6438 | 0.9431 | 0.8726 | 98.1843 |
| 10 | 0 | 30 | 97.0222 | 0.7906 | 2.9778 | 98.1322 | 0.2946 | 1.5732 | 0.8602 | 0.8681 | 98.2718 |
| 2 | 0 | 30 | 97.0579 | 0.7927 | 2.9421 | 98.0652 | 0.3017 | 1.6331 | 0.9873 | 0.8763 | 98.1364 |
| 3 | 0 | 30 | 97.0086 | 0.8149 | 2.9914 | 98.0938 | 0.3004 | 1.6057 | 0.9251 | 0.8708 | 98.2040 |
| 4 | 0 | 30 | 97.0791 | 0.8085 | 2.9209 | 98.0894 | 0.2921 | 1.6185 | 0.8721 | 0.8753 | 98.2527 |
| 5 | 0 | 30 | 96.9528 | 0.7925 | 3.0472 | 98.1136 | 0.2960 | 1.5904 | 0.8359 | 0.8624 | 98.3017 |
| 6 | 0 | 30 | 97.0366 | 0.8108 | 2.9634 | 98.1143 | 0.2984 | 1.5873 | 0.7836 | 0.8730 | 98.3434 |
| 7 | 0 | 30 | 96.9816 | 0.7856 | 3.0184 | 98.1764 | 0.2726 | 1.5510 | 0.8663 | 0.8751 | 98.2586 |
| 8 | 0 | 30 | 96.8139 | 0.7921 | 3.1861 | 98.1565 | 0.3033 | 1.5402 | 0.8450 | 0.8630 | 98.2920 |
| 9 | 0 | 30 | 97.0271 | 0.7890 | 2.9729 | 98.0997 | 0.3187 | 1.5815 | 0.8139 | 0.8742 | 98.3119 |
| 1 | 0.5 | 30 | 96.2315 | 0.8252 | 3.7685 | 97.9119 | 0.3962 | 1.6919 | 1.6780 | 0.8866 | 97.4355 |
| 10 | 0.5 | 30 | 96.0490 | 0.7959 | 3.951 | 97.9683 | 0.3986 | 1.6331 | 1.8062 | 0.8945 | 97.2993 |
| 2 | 0.5 | 30 | 96.2847 | 0.8290 | 3.7153 | 97.9632 | 0.3987 | 1.6382 | 1.8285 | 0.8848 | 97.2867 |
| 3 | 0.5 | 30 | 96.3518 | 0.8252 | 3.6482 | 97.9067 | 0.4127 | 1.6806 | 1.6921 | 0.9035 | 97.4045 |
| 4 | 0.5 | 30 | 96.3188 | 0.8282 | 3.6812 | 97.9198 | 0.3943 | 1.6859 | 1.6482 | 0.9074 | 97.4444 |
| 5 | 0.5 | 30 | 96.3204 | 0.8357 | 3.6796 | 97.8766 | 0.4198 | 1.7036 | 1.8506 | 0.8597 | 97.2897 |
| 6 | 0.5 | 30 | 96.2870 | 0.8553 | 3.7130 | 97.9892 | 0.3589 | 1.6519 | 1.3118 | 0.9730 | 97.7152 |
| 7 | 0.5 | 30 | 96.1451 | 1.0269 | 3.8549 | 97.9354 | 0.4002 | 1.6644 | 2.3537 | 1.0161 | 96.6302 |
| 8 | 0.5 | 30 | 95.8405 | 0.8434 | 4.1595 | 98.0232 | 0.3438 | 1.6330 | 2.1094 | 0.8776 | 97.0130 |
| 9 | 0.5 | 30 | 96.2186 | 0.8169 | 3.7814 | 97.9392 | 0.3752 | 1.6856 | 1.8306 | 0.9038 | 97.2656 |
| 1 | 1 | 30 | 95.3235 | 1.0856 | 4.6765 | 97.6375 | 0.5011 | 1.8614 | 2.2566 | 0.9130 | 96.8304 |
| 2 | 1 | 30 | 95.3958 | 1.0749 | 4.6042 | 97.6628 | 0.5084 | 1.8288 | 2.2871 | 0.8910 | 96.8219 |
| 3 | 1 | 30 | 95.3970 | 1.0675 | 4.6030 | 97.6658 | 0.4975 | 1.8367 | 2.2306 | 0.9212 | 96.8482 |
| 4 | 1 | 30 | 95.4132 | 1.0703 | 4.5868 | 97.7577 | 0.4800 | 1.7623 | 2.1778 | 0.9172 | 96.9050 |

TABLE 31-continued

RP-HPLC, SEC and AEX Results

| Formulation | Time Point (Months) | Condition (° C.) | RP-HPLC % Main Peak | RP-HPLC % LURS | RP-HPLC % Total Impurities | SEC % Monomer | SEC % Total Aggregates | SEC % Total Fragments | AEX % TAV | AEX % TBV | AEX % Main Peak |
|---|---|---|---|---|---|---|---|---|---|---|---|
| 5 | 1 | 30 | 94.5836 | 1.1350 | 5.4164 | 97.6903 | 0.5176 | 1.7921 | 2.5329 | 0.8675 | 96.5997 |
| 6 | 1 | 30 | 95.2597 | 0.3775 | 4.7403 | 97.8162 | 0.4250 | 1.7589 | 1.9577 | 1.0294 | 97.0128 |
| 7 | 1 | 30 | 95.3225 | 1.1025 | 4.6775 | 97.6593 | 0.5144 | 1.8264 | 2.3890 | 0.8685 | 96.7426 |
| 8 | 1 | 30 | 93.9675 | 1.2007 | 6.0325 | 97.7444 | 0.4220 | 1.8335 | 2.6017 | 0.9102 | 96.4881 |
| 9 | 1 | 30 | 95.1285 | 0.8441 | 4.8715 | 97.7774 | 0.4279 | 1.7947 | 2.1630 | 0.9140 | 96.9230 |
| 10 | 1 | 30 | 95.3148 | 1.0760 | 4.6852 | 97.6399 | 0.5092 | 1.8509 | 2.2527 | 0.8837 | 96.8636 |
| 1 | 1 | 5 | 96.6494 | 0.7934 | 3.3506 | 98.0703 | 0.3194 | 1.6103 | 1.0544 | 0.8740 | 98.0716 |
| 2 | 1 | 5 | 96.6817 | 0.7972 | 3.3183 | 98.0919 | 0.3207 | 1.5874 | 1.0349 | 0.8858 | 98.0793 |
| 3 | 1 | 5 | 96.6297 | 0.7941 | 3.3703 | 98.1229 | 0.3138 | 1.5633 | 1.0521 | 0.8917 | 98.0561 |
| 4 | 1 | 5 | 96.7693 | 0.7812 | 3.2307 | 98.1862 | 0.3016 | 1.5122 | 1.0107 | 0.8948 | 98.0945 |
| 5 | 1 | 5 | 96.5000 | 0.7975 | 3.5000 | 98.0984 | 0.3303 | 1.5713 | 1.1433 | 0.889 | 97.9677 |
| 6 | 1 | 5 | 96.7569 | 0.7964 | 3.2431 | 98.1742 | 0.3018 | 1.524 | 0.902 | 0.9036 | 98.1944 |
| 7 | 1 | 5 | 96.6277 | 0.797 | 3.3723 | 98.1321 | 0.3249 | 1.543 | 1.0877 | 0.8701 | 98.0422 |
| 8 | 1 | 5 | 98.7298 | 0.805 | 3.2702 | 98.1508 | 0.3104 | 1.5388 | 1.1318 | 0.8399 | 98.0083 |
| 9 | 1 | 5 | 96.6083 | 0.7974 | 3.3917 | 98.1532 | 0.3318 | 1.515 | 0.9621 | 0.876 | 98.1619 |
| 10 | 1 | 5 | 96.1705 | 0.8012 | 3.8295 | 98.1094 | 0.3209 | 1.5697 | 1.0447 | 0.8813 | 98.074 |
| 1 | 2 | 30 | 93.3779 | 1.0833 | 6.6221 | 97.1541 | 0.8639 | 1.9821 | 4.1438 | 0.9143 | 94.9418 |
| 2 | 2 | 30 | 93.3437 | 1.0659 | 6.6563 | 97.2536 | 0.845 | 1.9014 | 4.1228 | 0.9188 | 94.9583 |
| 3 | 2 | 30 | 93.8092 | 1.0446 | 6.1908 | 97.3284 | 0.816 | 1.8556 | 4.0431 | 0.9112 | 95.0437 |
| 4 | 2 | 30 | 93.8144 | 1.0654 | 6.1856 | 97.4325 | 0.7471 | 1.8204 | 3.8913 | 0.9243 | 95.1844 |
| 5 | 2 | 30 | 92.3537 | 1.9436 | 7.6463 | 97.2475 | 0.866 | 1.8866 | 4.4245 | 0.847 | 94.7286 |
| 6 | 2 | 30 | 94.2372 | 1.1781 | 5.7628 | 97.6187 | 0.5873 | 1.794 | 3.3332 | 1.0857 | 95.581 |
| 7 | 2 | 30 | 92.6763 | 1.8782 | 7.3237 | 97.3474 | 0.7921 | 1.8606 | 4.2778 | 0.8471 | 94.8751 |
| 8 | 2 | 30 | 91.3556 | 2.0808 | 8.6444 | 97.4875 | 0.5916 | 1.9209 | 4.4336 | 0.9409 | 94.6254 |
| 9 | 2 | 30 | 93.286 | 1.1269 | 6.714 | 97.3741 | 0.5655 | 2.0604 | 3.862 | 1.0084 | 95.1296 |
| 10 | 2 | 30 | 93.3924 | 1.0613 | 6.6076 | 97.1784 | 0.8142 | 2.0074 | 4.1756 | 0.8949 | 94.9295 |
| 1 | 2 | 5 | 96.8953 | 0.7234 | 3.1047 | 98.1709 | 0.347 | 1.4821 | 1.307 | 0.8542 | 97.8388 |
| 2 | 2 | 5 | 96.9896 | 0.7324 | 3.0104 | 98.1537 | 0.3519 | 1.4944 | 1.2109 | 0.8567 | 97.9324 |
| 3 | 2 | 5 | 96.9962 | 0.728 | 3.0038 | 93.1516 | 0.3528 | 1.4955 | 1.275 | 0.8716 | 97.8535 |
| 4 | 2 | 5 | 96.9633 | 0.7258 | 3.0367 | 98.2226 | 0.3289 | 1.4485 | 1.3099 | 0.8625 | 97.8276 |
| 5 | 2 | 5 | 96.8466 | 0.7346 | 3.1534 | 98.1578 | 0.3438 | 1.4985 | 1.4457 | 0.8503 | 97.704 |
| 6 | 2 | 5 | 97.0824 | 0.7363 | 2.9176 | 98.1757 | 0.3219 | 1.5024 | 1.1531 | 0.866 | 97.9809 |
| 7 | 2 | 5 | 96.8699 | 0.7350 | 3.1301 | 98.2028 | 0.3354 | 1.4619 | 1.4767 | 0.8591 | 97.6642 |
| 8 | 2 | 5 | 96.9530 | 0.7498 | 3.0470 | 93.1819 | 0.3481 | 1.4700 | 1.4784 | 0.8475 | 97.6742 |
| 9 | 2 | 5 | 96.827 | 0.7422 | 3.1730 | 98.1345 | 0.3437 | 1.5219 | 1.2891 | 0.8539 | 97.8570 |
| 10 | 2 | 5 | 96.8821 | 0.7329 | 3.1179 | 98.1899 | 0.3510 | 1.4591 | 1.2979 | 0.8611 | 97.841 |
| 1 | 3 | 30 | 90.5893 | 1.8609 | 9.4107 | 95.4619 | 1.3365 | 3.1816 | 6.4557 | 1.2244 | 92.3199 |
| 2 | 3 | 30 | 90.6977 | 1.8311 | 9.3023 | 95.8192 | 1.2081 | 2.9727 | 6.0495 | 1.029 | 92.9215 |
| 3 | 3 | 30 | 91.0457 | 1.8134 | 8.9543 | 95.8828 | 1.2027 | 2.9144 | 5.8713 | 1.0455 | 93.0832 |
| 4 | 3 | 30 | 91.2988 | 1.8260 | 8.7012 | 96.0930 | 1.0589 | 2.8480 | 5.5009 | 1.1993 | 93.2997 |
| 5 | 3 | 30 | 89.0961 | 2.3881 | 10.9039 | 95.9943 | 1.2320 | 2.7537 | 6.7889 | 1.1934 | 92.0177 |
| 6 | 3 | 30 | 92.1509 | 1.7257 | 7.8491 | 96.6058 | 0.7486 | 2.6456 | 4.5793 | 1.448 | 93.9727 |
| 7 | 3 | 30 | 89.6819 | 2.3004 | 10.3131 | 96.0146 | 1.1406 | 2.8448 | 6.2754 | 1.0358 | 92.6888 |

TABLE 32

HIAC and MFI Results

| Batch | Time-point (Months) | Condition (° C.) | HIAC >=10 um Average | HIAC >=2 um Average | HIAC >=25 um Average | HIAC >=5 um Average | MFI >=2 um | MFI >5 um | MFI >=5 um and <0.85 AR | MFI >5 um and >=0.85 AR | MFI Circular Particle Fraction |
|---|---|---|---|---|---|---|---|---|---|---|---|
| 1 | 0 | Initial | 658 | 19194 | 3 | 4457 | 119589 | 10862 | 653 | 10208 | 0.94 |
| 1 | 0.5 | 30° C. | 526 | 17306 | 18 | 4747 | 53219 | 6938 | 506 | 6432 | 0.93 |
| 1 | 1 | 30° C. | 628 | 14690 | 7 | 3454 | 61573 | 5657 | 288 | 5369 | 0.95 |
| 1 | 1 | 5° C. | 507 | 18542 | 3 | 3604 | 40115 | 2930 | 95 | 2835 | 0.97 |
| 1 | 2 | 30° C. | 936 | 16779 | 9 | 5833 | 53636 | 9445 | 434 | 9011 | 0.95 |
| 1 | 2 | 5° C. | 373 | 18423 | 5 | 3274 | 52554 | 4445 | 167 | 4278 | 0.96 |
| 1 | 3 | 30° C. | 998 | 38010 | 12 | 11198 | 154448 | 22579 | 1201 | 21378 | 0.95 |
| 1 | 3 | 5° C. | 1032 | 25229 | 9 | 7037 | 130370 | 10606 | 693 | 9914 | 0.93 |
| 1 | 6 | 30° C. | 402 | 5548 | 9 | 1617 | 23095 | 3271 | 197 | 3074 | 0.94 |
| 1 | 6 | 5° C. | 280 | 2952 | 6 | 668 | 12064 | 866 | 33 | 834 | 0.96 |
| 10 | 0 | Initial | 966 | 30483 | 1 | 7831 | 152248 | 11754 | 801 | 10954 | 0.93 |
| 10 | 0.5 | 30° C. | 484 | 13688 | 0 | 3540 | 69285 | 5868 | 287 | 5582 | 0.95 |
| 10 | 1 | 30° C. | 466 | 18668 | 1 | 3990 | 102674 | 7717 | 549 | 7169 | 0.93 |
| 10 | 1 | 5° C. | 333 | 17050 | 0 | 2598 | 54008 | 2496 | 116 | 2380 | 0.95 |
| 10 | 2 | 30° C. | 907 | 25473 | 8 | 6343 | 102279 | 9139 | 596 | 8543 | 0.93 |

TABLE 32-continued

HIAC and MFI Results

| Batch | Time-point (Months) | Condition (° C.) | HIAC >=10 um Average | HIAC >=2 um Average | HIAC >=25 um Average | HIAC >=5 um Average | MFI >=2 um | MFI >5 um | MFI >=5 um and <0.85 AR | MFI >5 um and >=0.85 AR | MFI Circular Particle Fraction |
|---|---|---|---|---|---|---|---|---|---|---|---|
| 10 | 2 | 5° C. | 446 | 15169 | 1 | 3428 | 52478 | 3880 | 152 | 3728 | 0.96 |
| 10 | 3 | 30° C. | 1186 | 26805 | 6 | 7964 | 283698 | 29431 | 2717 | 26714 | 0.91 |
| 10 | 3 | 5° C. | 958 | 22482 | 3 | 5821 | 122596 | 9753 | 627 | 9126 | 0.94 |
| 10 | 6 | 30° C. | 235 | 2217 | 14 | 651 | 21960 | 1818 | 85 | 1733 | 0.95 |
| 10 | 6 | 5° C. | 407 | 6249 | 4 | 1700 | 22916 | 1015 | 59 | 956 | 0.94 |
| 2 | 0 | Initial | 1279 | 31128 | 18 | 8912 | 100703 | 11889 | 645 | 11243 | 0.95 |
| 2 | 0.5 | 30° C. | 462 | 20072 | 1 | 4511 | 113899 | 11810 | 516 | 11294 | 0.96 |
| 2 | 1 | 30° C. | 1444 | 30151 | 14 | 9981 | 87398 | 12510 | 352 | 12157 | 0.97 |
| 2 | 1 | 5° C. | 375 | 11149 | 2 | 2109 | 59462 | 4940 | 328 | 4612 | 0.93 |
| 2 | 2 | 30° C. | 777 | 27703 | 7 | 6235 | 79060 | 11881 | 393 | 11488 | 0.97 |
| 2 | 2 | 5° C. | 380 | 12409 | 3 | 2672 | 90130 | 11751 | 478 | 11273 | 0.96 |
| 2 | 3 | 30° C. | 717 | 24912 | 15 | 6222 | 84309 | 10657 | 486 | 10171 | 0.95 |
| 2 | 3 | 5° C. | 259 | 10171 | 5 | 2074 | 36328 | 1893 | 129 | 1764 | 0.93 |
| 2 | 6 | 30° C. | 1036 | 6689 | 46 | 2763 | 20081 | 4722 | 167 | 4555 | 0.96 |
| 2 | 6 | 5° C. | 630 | 4861 | 28 | 1400 | 21316 | 2331 | 66 | 2265 | 0.97 |
| 3 | 0 | Initial | 890 | 26046 | 0 | 7153 | 85996 | 3806 | 269 | 3538 | 0.93 |
| 3 | 0.5 | 30° C. | 387 | 16646 | 4 | 3470 | 61773 | 5177 | 198 | 4979 | 0.96 |
| 3 | 1 | 30° C. | 500 | 17237 | 4 | 4229 | 73123 | 7088 | 267 | 6821 | 0.96 |
| 3 | 1 | 5° C. | 309 | 11407 | 2 | 2177 | 48051 | 3269 | 149 | 3120 | 0.95 |
| 3 | 2 | 30° C. | 1660 | 37369 | 8 | 11411 | 123708 | 21658 | 803 | 20856 | 0.96 |
| 3 | 2 | 5° C. | 360 | 11941 | 2 | 2583 | 50274 | 3868 | 170 | 3698 | 0.96 |
| 3 | 3 | 30° C. | 777 | 26716 | 9 | 7071 | 96666 | 9727 | 568 | 9159 | 0.94 |
| 3 | 3 | 5° C. | 581 | 19011 | 5 | 4454 | 85885 | 10156 | 477 | 9679 | 0.95 |
| 3 | 6 | 30° C. | 80 | 1503 | 3 | 328 | 19015 | 2905 | 296 | 2609 | 0.9 |
| 3 | 6 | 5° C. | 311 | 3771 | 1 | 1012 | 21087 | 3403 | 92 | 3312 | 0.97 |
| 4 | 0 | Initial | 707 | 26858 | 1 | 6921 | 72345 | 4827 | 257 | 4569 | 0.95 |
| 4 | 0.5 | 30° C. | 429 | 12156 | 1 | 2754 | 78855 | 6743 | 310 | 6433 | 0.95 |
| 4 | 1 | 30° C. | 965 | 26942 | 3 | 7338 | 67856 | 7043 | 306 | 6736 | 0.96 |
| 4 | 1 | 5° C. | 159 | 7921 | 4 | 1353 | 46186 | 3792 | 179 | 3613 | 0.95 |
| 4 | 2 | 30° C. | 1235 | 29861 | 6 | 8803 | 102443 | 10579 | 613 | 9966 | 0.94 |
| 4 | 2 | 5° C. | 433 | 13617 | 4 | 2828 | 72762 | 7090 | 385 | 6705 | 0.95 |
| 4 | 3 | 30° C. | 295 | 15993 | 7 | 3605 | 61532 | 7203 | 341 | 6862 | 0.95 |
| 4 | 3 | 5° C. | 605 | 17368 | 5 | 4010 | 85539 | 7439 | 434 | 7005 | 0.94 |
| 4 | 6 | 30° C. | 359 | 3022 | 21 | 1074 | 14162 | 2244 | 87 | 2157 | 0.96 |
| 4 | 6 | 5° C. | 482 | 4325 | 14 | 1458 | 13378 | 2275 | 146 | 2129 | 0.94 |
| 5 | 0 | Initial | 206 | 22708 | 0 | 3856 | 86515 | 6397 | 314 | 6083 | 0.95 |
| 5 | 0.5 | 30° C. | 370 | 13693 | 2 | 3312 | 79019 | 6043 | 395 | 5649 | 0.93 |
| 5 | 1 | 30° C. | 460 | 17267 | 2 | 3645 | 71144 | 5423 | 313 | 5110 | 0.94 |
| 5 | 1 | 5° C. | 195 | 15720 | 1 | 2092 | 45940 | 2815 | 136 | 2679 | 0.95 |
| 5 | 2 | 30° C. | 473 | 16801 | 2 | 3401 | 76115 | 4625 | 373 | 4252 | 0.92 |
| 5 | 2 | 5° C. | 492 | 14044 | 1 | 2992 | 49784 | 4818 | 231 | 4587 | 0.95 |
| 5 | 3 | 30° C. | 584 | 17953 | 3 | 5094 | 123626 | 11343 | 727 | 10616 | 0.94 |
| 5 | 3 | 5° C. | 303 | 12220 | 0 | 2632 | 88227 | 4990 | 395 | 4596 | 0.92 |
| 5 | 6 | 30° C. | 236 | 2099 | 13 | 573 | 11591 | 1212 | 129 | 1083 | 0.89 |
| 5 | 6 | 5° C. | 105 | 1621 | 8 | 261 | 12808 | 483 | 28 | 455 | 0.94 |
| 6 | 0 | Initial | 1267 | 36318 | 1 | 11017 | 103484 | 6047 | 477 | 5570 | 0.92 |
| 6 | 0.5 | 30° C. | 1282 | 23890 | 2 | 6644 | 111839 | 8988 | 916 | 8073 | 0.9 |
| 6 | 1 | 30° C. | 1167 | 24307 | 4 | 6011 | 98953 | 8844 | 657 | 8187 | 0.93 |
| 6 | 1 | 5° C. | 616 | 28416 | 4 | 5086 | 144570 | 8608 | 763 | 7845 | 0.91 |
| 6 | 2 | 30° C. | 608 | 22938 | 5 | 4250 | 75806 | 8641 | 447 | 8194 | 0.95 |
| 6 | 2 | 5° C. | 339 | 20314 | 2 | 3061 | 98897 | 5269 | 398 | 4871 | 0.92 |
| 6 | 3 | 30° C. | 970 | 35147 | 4 | 9310 | 171661 | 10028 | 961 | 9067 | 0.9 |
| 6 | 3 | 5° C. | 370 | 16967 | 1 | 2709 | 124366 | 5166 | 519 | 4646 | 0.9 |
| 6 | 6 | 30° C. | 773 | 6147 | 28 | 2232 | 26143 | 4751 | 347 | 4404 | 0.93 |
| 6 | 6 | 5° C. | 532 | 4068 | 20 | 1446 | 26129 | 3605 | 185 | 3420 | 0.95 |
| 7 | 0 | Initial | 708 | 22673 | 1 | 5399 | 68537 | 6702 | 336 | 6366 | 0.95 |
| 7 | 0.5 | 30° C. | 838 | 31506 | 1 | 6672 | 149040 | 24077 | 1096 | 22982 | 0.95 |
| 7 | 1 | 30° C. | 595 | 26083 | 6 | 6542 | 157117 | 17747 | 984 | 16763 | 0.94 |
| 7 | 1 | 5° C. | 413 | 11560 | 5 | 2953 | 52583 | 3975 | 133 | 3842 | 0.97 |
| 7 | 2 | 30° C. | 448 | 21403 | 1 | 4622 | 82936 | 6699 | 472 | 6227 | 0.93 |
| 7 | 2 | 5° C. | 802 | 21887 | 2 | 4941 | 50231 | 4678 | 177 | 4501 | 0.96 |
| 7 | 3 | 30° C. | 461 | 24766 | 3 | 5601 | 121862 | 10551 | 668 | 9882 | 0.94 |
| 7 | 3 | 5° C. | 301 | 14200 | 1 | 2470 | 85613 | 5591 | 277 | 5315 | 0.95 |
| 7 | 6 | 30° C. | 254 | 2452 | 11 | 608 | 18859 | 1192 | 75 | 1117 | 0.94 |
| 7 | 6 | 5° C. | 292 | 2774 | 10 | 590 | 22873 | 1150 | 44 | 1106 | 0.96 |
| 8 | 0 | Initial | 470 | 25128 | 1 | 4415 | 77574 | 5215 | 357 | 4858 | 0.93 |
| 8 | 0.5 | 30° C. | 1373 | 27710 | 3 | 6793 | 86291 | 6651 | 575 | 6076 | 0.91 |
| 8 | 1 | 30° C. | 979 | 18816 | 5 | 5662 | 45202 | 4943 | 224 | 4719 | 0.95 |
| 8 | 1 | 5° C. | 458 | 14278 | 0 | 2192 | 53161 | 1988 | 118 | 1870 | 0.94 |
| 8 | 2 | 30° C. | 794 | 16325 | 1 | 4426 | 84938 | 8600 | 560 | 8040 | 0.93 |
| 8 | 2 | 5° C. | 728 | 17815 | 3 | 4277 | 55084 | 4147 | 539 | 3608 | 0.87 |

TABLE 32-continued

HIAC and MFI Results

| | | | HIAC | | | | MFI | | | | |
|---|---|---|---|---|---|---|---|---|---|---|---|
| Batch | Time-point (Months) | Condition (° C.) | >=10 um Average | >=2 um Average | >=25 um Average | >=5 um Average | >=2 um | >5 um | >=5 um and <0.85 AR | >5 um and >=0.85 AR | Circular Particle Fraction |
| 8 | 3 | 30° C. | 870 | 25530 | 0 | 6413 | 125958 | 10770 | 667 | 10104 | 0.94 |
| 8 | 3 | 5° C. | 295 | 10722 | 2 | 2139 | 72289 | 4799 | 300 | 4499 | 0.94 |
| 8 | 6 | 30° C. | 381 | 5416 | 12 | 1373 | 20780 | 1756 | 151 | 1605 | 0.91 |
| 8 | 6 | 5° C. | 528 | 6736 | 5 | 1660 | 43199 | 2476 | 146 | 2331 | 0.94 |
| 9 | 0 | Initial | 850 | 28077 | 10 | 6845 | 60777 | 7103 | 249 | 6854 | 0.96 |
| 9 | 0.5 | 30° C. | 175 | 5265 | 0 | 815 | 50944 | 3217 | 172 | 3045 | 0.95 |
| 9 | 1 | 30° C. | 593 | 12558 | 4 | 3520 | 59544 | 3872 | 278 | 3593 | 0.93 |
| 9 | 1 | 5° C. | 285 | 7625 | 2 | 1503 | 56249 | 4596 | 185 | 4411 | 0.96 |
| 9 | 2 | 30° C. | 377 | 16774 | 2 | 2607 | 99134 | 8746 | 390 | 8356 | 0.96 |
| 9 | 2 | 5° C. | 475 | 12070 | 3 | 2748 | 125986 | 10721 | 572 | 10149 | 0.95 |
| 9 | 3 | 30° C. | 503 | 16033 | 1 | 3664 | 164713 | 13990 | 922 | 13068 | 0.93 |
| 9 | 3 | 5° C. | 189 | 11184 | 1 | 1891 | 70900 | 3690 | 198 | 3492 | 0.95 |
| 9 | 6 | 30° C. | 792 | 5204 | 30 | 1892 | 21123 | 1803 | 98 | 1705 | 0.95 |
| 9 | 6 | 5° C. | 479 | 6561 | 8 | 2192 | 34598 | 4135 | 144 | 3991 | 0.97 |

Physical Stability

Physical appearance data and visible particulates are consistent across all formulations, conditions, and time points. No visible particulates are reported. Solutions remain clear and colorless. Data is presented in Table 30.

Size Exclusion Chromatography (SEC)

The SEC percent monomer values and total aggregate values of all study formulations are presented in Table 31 from the 5° C. and 30° C. storage conditions. Stability data are available for up to 6 months of storage. The data shows that loss of monomer is primarily due to fragmentation. The SEC total fragments values of all study formulations are presented in Table 31 from the 5° C. and 30° C. storage conditions.

Anion Exchange Chromatography (AEX)

The AEX main peak values, TAV values and TBV values of all study formulations are presented in Table 31 from the 5° C. and 30° C. storage conditions.

RP-HPLC

RP-HPLC results show pH as having the greatest impact on stability, with high pH resulting in higher levels of degradation. The RP-HPLC main peak values and total impurities of all study formulations are presented in Table 31 from the 5° C. and 30° C. storage conditions.

Particulates

Particulates data measured by HIAC light obscuration and MFI at each time point and condition for all formulations are shown in Table 32 and show differences related to method variability. No specific trends are observed relative to the formulation factors. MFI is used to further characterize the particulate matter in each formulation to determine the morphology of the particles. Table 32 shows a comparison between particulate mean value of all formulations for particulate matter data≥5 μm as compared with particulate matter data≥5 μm with an aspect ratio (AR)<0.85. Particulates with AR<0.85 are considered to be non-spherical and are more likely protein-related aggregates. The results show a significant difference between the raw particulates data at ≥5 μm with the ≥5 μm particulates data with the AR taken into consideration. These data imply that many of the particulates in solution are spherical and likely due to silicone oil droplets, a common phenomenon in the prefilled syringe system. The circular particle fraction results support this conclusion, given that the circular particle fraction for all formulations was >90%.

Conclusion: Data from all formulations studied showed similar stability profiles over the course of the study. The study shows the formulation is stable at pH ranging from 7 to 8 and concentrations ranging from 1 to 30 mg/mL.

SEQUENCES

The following amino acid sequences are referred to in the disclosure and are provided below for reference.

Incretin Analog/GGG Tri-Receptor Agonist
SEQ ID NO: 1
Y-Aib-QGTFTSDYSI-αMeL-LDKK((2-[2-(2-amino-ethoxy)-ethoxy]-acetyl)-(γGlu)-CO-$(CH_2)_{18}$-$CO_2H$)AQ-Aib-AFIEYLLEGGPSSGAPPPS-$NH_2$ human GIP
SEQ ID NO: 2
YAEGTFISDYSIAMDKIHQQDFVNWLLAQKGKKNDWKHNITQ human GLP-$1_{7-36}$ amide
SEQ ID NO: 3
HAEGTFTSDVSSYLEGQAAKEFIAWLVKGR-$NH_2$ human GCG
SEQ ID NO: 4
HSQGTFTSDYSKYLDSRRAQDFVQWLMNT

The invention claimed is:

1. A pharmaceutical composition comprising:

an incretin analog comprising SEQ ID NO:1, or pharmaceutically acceptable salt thereof at a concentration from about 1 mg/mL to about 30 mg/mL;

a tris(hydroxymethyl)aminomethane (TRIS) buffer at a concentration from about 10 mM to about 100 mM;

mannitol at a concentration from about 10 mg/mL to about 100 mg/mL; and an optional preservative selected from the group consisting of m-cresol and phenol;

wherein the pharmaceutical composition has a pH of about 6.5 to about 7.5.

2. The pharmaceutical composition of claim 1, wherein the mannitol is at a concentration of about 48 mg/mL.

3. The pharmaceutical composition of claim 1, wherein the optional preservative is m-cresol and is at a concentration of from about 1 mg/mL to about 10 mg/mL.

4. The pharmaceutical composition of claim 3, wherein the m-cresol is at a concentration of 3.15 mg/mL.

5. The pharmaceutical composition of claim 1, wherein the optional preservative is phenol and is at a concentration of from about 1 mg/mL to about 10 mg/mL.

6. The pharmaceutical composition of claim 5, wherein the phenol is at a concentration of 5 mg/mL.

7. The pharmaceutical composition of claim 1, wherein the incretin analog is at a concentration selected from the group consisting of 1 mg/mL, 2 mg/mL, 3 mg/mL, 4 mg/mL, 5 mg/mL, 6 mg/mL, 8 mg/mL, 9 mg/mL, 12 mg/mL, 18 mg/mL, 24 mg/mL and 30 mg/mL.

8. The pharmaceutical composition of claim 1, wherein the TRIS buffer is at a concentration of about 10 mM.

9. The pharmaceutical composition of claim 1 further comprising ethylenediaminetetraacetic acid (EDTA) at a concentration of 0.3 mg/mL.

10. The pharmaceutical composition of claim 1, wherein mannitol is at a concentration of 48 mg/mL.

11. The pharmaceutical composition of claim 10, wherein the incretin analog or pharmaceutically acceptable salt thereof is at a concentration selected from the group consisting of 1 mg/mL, 2 mg/mL, 3 mg/mL, 4 mg/mL, 5 mg/mL, 6 mg/mL, 8 mg/mL, 9 mg/mL, 12 mg/mL, 18 mg/mL, 24 mg/mL and 30 mg/mL.

12. The pharmaceutical composition of claim 1 further comprising a preservative selected from the group consisting of m-cresol and phenol, wherein the preservative is at a concentration of about 1 mg/mL to about 10 mg/mL.

13. The pharmaceutical composition of claim 1 further comprising a pharmaceutically acceptable carrier, diluent or excipient.

14. The pharmaceutical composition of claim 1, wherein the pharmaceutically acceptable salt is a sodium salt.

15. The pharmaceutical composition of claim 1, wherein the pharmaceutically acceptable salt is a tetra sodium salt.

16. A method of treating diabetes comprising the step of: administering to an individual in need thereof an effective dose of the pharmaceutical composition of claim 1.

17. The method of claim 16, wherein the effective dose is administered using an automatic injection apparatus.

18. The method of claim 16, wherein the effective dose is administered once weekly.

19. A method of treating obesity comprising the step of: administering to an individual in need thereof an effective dose of the pharmaceutical composition of claim 1.

20. The method of claim 19, wherein the effective dose is administered using an automatic injection apparatus.

21. The method of claim 19, wherein the effective dose is administered once weekly.

22. An article of manufacture comprising the pharmaceutical composition of claim 1, wherein the article of manufacture is selected from a multiuse vial, a reusable pen injector, a pre-filled disposable pen, an autoinjector, and a pump.

23. The method of claim 21, wherein the volume of the pharmaceutical composition administered is about 0.5 mL.

24. A pharmaceutical composition comprising:

an incretin analog comprising SEQ ID NO:1, or pharmaceutically acceptable salt thereof at a concentration from about 1 mg/mL to about 30 mg/ml;

a tris(hydroxymethyl)aminomethane (TRIS) buffer at a concentration of about 10 mM;

mannitol at a concentration of about 48 mg/mL; and an optional preservative selected from the group consisting of m-cresol and phenol;

wherein the pharmaceutical composition has a pH of about 7.5.

25. A pharmaceutical composition comprising:

an incretin analog comprising SEQ ID NO:1, or pharmaceutically acceptable salt thereof, at a concentration from about 1 mg/mL to about 30 mg/ml;

a tris(hydroxymethyl)aminomethane (TRIS) buffer at a concentration of about 10 mM;

mannitol at a concentration from about 10 mg/mL to about 100 mg/ml; and phenol at a concentration of about 5 mg/ml;

wherein the pharmaceutical composition has a pH of about 7.5.

* * * * *

SEQUENCE LISTING

<160> NUMBER OF SEQ ID NOS: 4

<210> SEQ ID NO 1
<211> LENGTH: 39

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leucine
<220> FEATURE:
<221> NAME/KEY: MOD_RES
<222> LOCATION: (17)..(17)
<223> OTHER INFORMATION: Lys at position 17 is chemically modified
      through conjugation to the epsilon-amino group of the K side-chain
      with (2-[2-(2-Amino-ethoxy)-ethoxy]-acetyl)-(gamma-Glu)-CO-
      (CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 1

Tyr Xaa Gln Gly Thr Phe Thr Ser Asp Tyr Ser Ile Xaa Leu Asp Lys
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
        35


<210> SEQ ID NO 2
<211> LENGTH: 42
<212> TYPE: PRT
<213> ORGANISM: Homo sapiens

<400> SEQUENCE: 2

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40


<210> SEQ ID NO 3
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30


<210> SEQ ID NO 4
<211> LENGTH: 29
<212> TYPE: PRT
<213> ORGANISM: Homo sapiens
```

-continued

```
<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```